United States Patent
Mousa et al.

(10) Patent No.: US 8,607,989 B2
(45) Date of Patent: Dec. 17, 2013

(54) FILTER COMPOSITES FOR DRUG DETOXIFICATION

(75) Inventors: Shaker A. Mousa, Wynantskill, NY (US); Robert J. Linhardt, Albany, NY (US)

(73) Assignee: Vascular Vision Pharmaceutical Co., Rensselaer, NY (US)

( * ) Notice: Subject to any disclaimer, the term of this patent is extended or adjusted under 35 U.S.C. 154(b) by 560 days.

(21) Appl. No.: 12/815,453

(22) Filed: Jun. 15, 2010

(65) Prior Publication Data

US 2010/0316694 A1 Dec. 16, 2010

Related U.S. Application Data

(60) Provisional application No. 61/268,626, filed on Jun. 15, 2009.

(51) Int. Cl.
*B01D 37/00* (2006.01)
*A61K 9/70* (2006.01)
*A61K 31/727* (2006.01)
*B01D 29/00* (2006.01)

(52) U.S. Cl.
USPC ........... 210/490; 210/782; 210/645; 210/504; 210/506; 210/694; 210/767; 514/56; 977/742

(58) Field of Classification Search
USPC ......... 210/488–490, 767, 782, 645, 503–506, 210/694; 424/443; 977/742; 427/2.3; 514/56
See application file for complete search history.

(56) References Cited

U.S. PATENT DOCUMENTS

| | | | |
|---|---|---|---|
| 4,048,064 A | | 9/1977 | Clark, III |
| 5,935,436 A | * | 8/1999 | Lee et al. .................. 210/257.1 |
| 7,419,601 B2 | * | 9/2008 | Cooper et al. ............... 210/679 |
| 2002/0158007 A1 | * | 10/2002 | Li ............................ 210/497.01 |

OTHER PUBLICATIONS

Jemal A, et al; Cancer Statistics, 2003. CA-A Cancer Journal for Clinicians, vol. 53, No. 1; Jan./Feb. 2003. pp. 5-26.
Chang et al.; The National Cancer Data Base Report on Cutaneous and Noncutaneous Melanoma: A Summary of 84,836 Cases from the Past Decade. 1998 American Cancer Society. pp. 1664-1678.
Pingpank et al.; Phase I Study of Hepatic Arterial Melphalan Infusion and Hepatic Venous Hemofiltration Using Percutaneously Placed Catheters in Patients with Unresectable Hepatic Malignancies. Journal of Clinical Oncology, vol. 23, No. 15, May 20, 2005. pp. 3465-3474.

(Continued)

*Primary Examiner* — Benjamin Kurtz
*Assistant Examiner* — Madeline Gonzalez
(74) *Attorney, Agent, or Firm* — Schmeiser, Olsen & Watts, LLP

(57) ABSTRACT

A filter and a method of forming a suture structure. The filter includes layered structure(s) interior to the filter. Each layered structure includes a carbon structure comprising carbon and a coating on a surface of the carbon structure. Each layered structure may further include a heparin layer that includes heparin and is on the coating. The coating of the filter includes cellulose, PMMA, PEMA, or PHEMA. The carbon structure may include an activated charcoal layer or carbon nanotube(s). The layered structure is configured to remove a contaminant flowing through the filter. The method of forming the suture structure includes forming a film on a suture that has been previously formed on a mammal. The film includes both a coating on the suture and a heparin layer that includes heparin and is on the coating. The coating of the suture structure includes cellulose, PMMA, PEMA, or PHEMA.

24 Claims, 11 Drawing Sheets

(56) References Cited

OTHER PUBLICATIONS

Rothenberg et al.; Superiority of Oxaliplatin and Fluourouracil-Leucovorin Compared With Either Therapy Alone in Patients With Progressive Colorectal Cancer After Irinotecan and Fluorouracil-Leucovorin: Interim Results of a Phase III Trial. Journal of Clinical Oncology, vol. 21, No. 11 (Jun. 1, 2003). pp. 2059-2069.

Kemeny et al.; Phase I Study of Hepatic Arterial Infusion of Floxuridine and Dexamethasone With Systemic Irinotecan for Unresectable Hepatic Metastases From Colorectal cancer. Journal of Clinical Oncology, vol. 19, No. 10 (May 15, 2001). pp. 2687-2695.

Egan et al.; Epidemiologic Aspects of Uveal Melanoma. Survey of Ophthalmology, vol. 32, No. 4, Jan.-Feb. 1988. pp. 239-251.

Gragoudas et al.; Survival of Patients with Metastases from Uveal Melanoma. Ophthalmology, vol. 98, No. 3, Mar. 1991. pp. 383-390.

Kath et al.; Prognosis and Treatment of Disseminated Uveal Melanoma. Cancer, vol. 72, No. 7, Oct. 1, 1993. pp. 2219-2223.

Eckman et al.; A Critical Evaluation of the Principles Governing the Advantages of Intra-arterial Infusions. Journal of Pharmacokinetics and Biopharmaceutics, vol. 2, No. 3, 1974. pp. 257-285.

Vermorken, JG; The role of chemotherapy in squamous cell carcinoma of the uterine cervix: a review. Int J Gynecol Cancer, 1993, 3. pp. 129-142.

Kusunoki et al.; Effect of Sodium Thiosulfate on Cisplatin Removal With Complete Hepatic Venous Isolation and Extracorporeal Charcoal Hemoperfusion: A Pharmacokinetic Evaluation. Annals of Surgical Oncology 8(5), 2001. pp. 449-457.

Tominaga et al.; Pharmacological evaluation of portal venous isolation and charcoal haemoperfusion for high-dose intra-arterial chemotherapy of the pancreas. British Journal of Surgery, 1997, 84. pp. 1072-1076.

Jones and Alexander. Development of Isolated Hepatic Perfusion for Patients Who Have Unresectable Hepatic Malignancies. Surgical Oncology Clinics of North America, 17, (2008). pp. 857-876.

Maruo et al.; Percutaneous Pelvic Perfusion with Extracorporeal Chemofiltration for Advanced Uterine Cervical Carcinoma. Surgical Oncology Clinics of North America 17, (2008). pp. 843-856.

Sigurdson ER, Ridge JA, Daly JM; Fluorodeoxyuridine uptake by human colorectal hepatic metastases after hepatic artery infusion. Surgery, 1986;100. pp. 285-291.

Yatzidis, H.; A Convenient Hemoperfusion Micro-Apparatus Over Charcoal for the Treatment of Endogenous and Exogenous Intoxications. Its use as an effective artificial kidney. Proceedings of the European Dialysis and Transplant Association, vol. 1, 1964. pp. 83-87.

Rosenbaum JL; Poisonings. In Giordano C ed. Sorbents and their clinical applications. New York: Academic Press, 1980. pp. 451-467.

Hagstam et al.; Experimental Studies on Charcoal Haemoperfusion in Phenobarbital Intoxication and Uraemia, Including Histopathological Findings. Acta Medica Scandinavica, vol. 180, fasc. 5, 1966. pp. 593-610.

Chang TM.; Therapeutic Applications of Polymeric Artificial Cells. Nature Reviews Drug Discovery, vol. 4, Mar. 2005. pp. 221-235.

Botella et al.; Adsorption in hemodialysis. Kidney International, vol. 58, Suppl 76, (2000). pp. S-60-S-65.

Hasirci and Akovali; Polymer coating for hemoperfusion over activated charcoal. Journal of biomedical Materials Research, vol. 20, (1986). pp. 963-970.

El-Kheshen et al.; Coating charcoal with polyacrylate-polymethacrylate copolymer for hemoperfusion. III: The effect of the coat thickness on the adsorption capacity of the coated charcoal and its adsorptivity to small and middle size molecules. J. Microencapsulation, 1995, vol. 12, No. 5. pp. 505-514.

Hanasawa, Kazuyoshi; Extracorporeal Treatment for Septic Patients: New Adsorption Technologies and Their Clinical Application. Therapeutic Apheresis 6(4), 2002. pp. 290-295.

Legallais et al.; The place of adsorption and bio-chromatography in extracorporeal liver support systems. Journal of Chromatography B Analyt Technol Biomed Life Sci. 861, (2008). pp. 171-176.

De Pont, Anne-Cornelie JM.; Extracorporeal treatment of intoxications. Curr Opin Crit Care 13, 2007. pp. 668-673.

Mikhalovsky, Sergey V.; Emerging technologies in extracorporeal treatment: focus on adsorption. Perfusion 2003; 18. pp. 47-54.

Bansal et al.; Active Carbon. New York, NY: Marcel Dekker, 1988. pp. 335-460.

Sangster et al; The Influence of Haemoperfusion on Haemostasis and Cellular Constituents of the Blood in the Treatment of Intoxications / A Comparative Study of Three Types of Columns (Haemocol, Amberlite XAD-4, Gambro Adsorba 300 C). Arch Toxicol (1981) 47. pp. 269-278.

Tabei et al.; Application of plasma perfusion in hepatic-failure. BiomatArt Cells Immob Biotech 19(1), 1991. pp. 193-201.

Webb, D.; Charcoal haemoperfusion in drug intoxication. Br JHosp Med 49, 1993. pp. 493-496.

Linhardt and Toida; Heparin Oligosaccharides: New Analogues Development and Applications (Z. J. Witczak and K. A. Nieforth, eds) Carbohydrates in Drug Design. Marcel Dekker, NY, 1997. pp. 277-341.

Larm et al.; Surface-immobilized heparin, in (D. A. Lane and U. Linhahl, eds) Heparin: Chemical and Biological Properties Clinical Applications. CRC Press, Boca Raton, 1989. pp. 597-608.

Brynda et al.; Albumin and heparin multilayer coatings for blood-contacting medical devices. JBiomed Mat Res 51, 2000. pp. 249-257.

Welton, Thomas; Room-Temperature Ionic Liquids. Solvents for Synthesis and Catalysis. Chem Rev 1999, 99. pp. 2071-2083.

Swatloski et al.; Dissolution of Cellulose with Ionic Liquids. J Am Cheml Soc 2002, 124. pp. 4974-4975.

Murugesan et al.; Blood Compatible Carbon Nanotubes—Nano-based Neoproteoglycans. Langmuir 2006, 22. pp. 3461-3463.

Murugesan et al.; Ionic Liquid Derived Blood Compatible Composite Membranes for Kidney Dialysis. JBiorned Mat Res: Part B—App Biornat 79B, 2006. pp. 298-304.

Park et al.; Heparin-cellulose-charcoal composites for drug detoxification prepared using room temperature ionic liquids, Chem Commun submitted, 2008. pp. 5022-5024.

Raymond et al.; Cellular and Molecular Pharmacology of Oxaliplatin. Molecular Cancer Therapeutics, vol. 1, Jan. 2002. pp. 227-235.

Cvitkovic, Esteban; A Historical Perspective on Oxaliplatin: Rethinking the Role of Platinum Compounds and Learning From Near Misses. Seminars in Oncology, vol. 25, No. 2, Suppl 5, Apr. 1998. pp. 1-3.

Raymond et al.; Oxaliplatin: A review of preclinical and clinical studies. Annals of Oncology 9, 1998. pp. 1053-1071.

Raymond et al.; Oxaliplatin: Mechanism of Action and Antineoplastic Activity. Seminars in Oncology, vol. 25, No. 2, Suppl 5, Apr. 1998. pp. 4-12.

Soulie et al.; Oxaliplatin: The first DACH platinum in clinical practice. Bull Cancer 1997; 84 (6). pp. 665-673. English Abstract.

Cvitkovic E.; Ongoing and unsaid on oxaliplatin: the hope. British Journal of Cancer (1998) 77 (Supplement 4). pp. 8-11.

Llory et al.; Feasibility of High-Dose Platinum Delivery With Combined Carboplatin and Oxaliplatin. Journal of the National Cancer Institute, vol. 86, No. 14, Jul. 20, 1994. pp. 1098-1099.

Soulie et al.; Oxaliplatin/cisplatin (L-OHP/CDDP) Combination in Heavily Pretreated Ovarian Cancer. European Journal of Cancer, vol. 33, No. 9, 1997. pp. 1400-1406.

Rixe et al.; Oxaliplatin, Tetraplatin, Cisplatin, and Carboplatin: Spectrum of Activity in Drug-Resistant Cell Lines and in the Cell Lines of the National Cancer Institute's Anticancer Drug Screen Panel. Biochemical Pharmacology, vol. 52, 1996. pp. 1855-1865.

Pendyala et al.; Cytotoxicity, cellular accumulation and DNA binding of oxaliplatin isomers. Cancer Letters 97 (1995). pp. 177-184.

Pendyala et al.; In Vitro Cytotoxicity, Protein Binding, Red Blood Cell Partitioning, and Biotransformation of Oxaliplatin. Cancer Research 53, Dec. 15, 1993. pp. 5970-5976.

Holmes et al.; Comparative Neurotoxicity of Oxaliplatin, Cisplatin, and Ormaplatin in a Wistar Rat Model. Journal of Toxicological Sciences 46, 1998. pp. 342-351.

Raymond et al. Activity of Oxaliplatin against Human Tumor Colony-forming Units. Clinical Cancer Research, vol. 4, Apr. 1998. pp. 1021-1029.

(56) References Cited

OTHER PUBLICATIONS

Hull et al.; Determination of Platinum in Serum and Ultrafiltrate by Flameless Atomic Absorption Spectrophotometry. Journal of Pharmaceutical Sciences, vol. 70, No. 5, May 1981. pp. 500-502.

Wissink et al.; Immobilization of heparin to EDC/NHS-crosslinked collagen. Characterization and in vitro evaluation. Biomaterials 22, (2001). pp. 151-163.

Bitter and Muir. A Modified Uronic Acid Carbazole Reaction. Analytical Biochemistry 4, (1962). pp. 330-334.

Nakamura et al.; Inhibitory Effect of Sorbitol on Acetaminophen Adsorption by Activated Carbon; J. Environ. Sci. Health, A37(5), (2002). pp. 905-912.

Melillo et al.; The effect of protein binding on ibuprofen adsorption to activated carbons; Carbon 42 (2004). pp. 565-571.

Sarnatskaya et al.; Albumin, Bilirubin, and Activated Carbon: New Edges of an Old Triangle. Art, Cells, Blood Subs., and Immob. Biotech., 30(2), (2002). pp. 113-126.

Mathur et al.; Activated Charcoal-Carboxy-methylcellulos Gel Formulation as an Antidotal Agent for Orally Ingested Aspirin; Am J Hosp Pharm 33, Jul. 1976. pp. 717-719.

Crome et al.; Experience with cellulose acetate-coated activated charcoal haemoperfusion in the treatment of severe hypnotic drug intoxication; Postgraduate Medical Journal (Nov. 1980) 56. pp. 763-766.

Peterson et al.; Cleansing the Blood—Hemodialysis, Peritoneal Dialysis, Exchange Transfusion, Charcoal Hemoperfusion, Forced Diuresis. Pediatric Clinics of North America, vol. 33, No. 3, Jun. 1986. pp. 675-689.

Winchester et al.; Sorbent Hemoperfusion in End-Stage Renal Disease: An In-Depth Review. Advances in Renal Replacement Therapy, vol. 9, No. 1, Jan. 2002. pp. 19-25.

Denti et al.; Adsorption Characteristics of Cellulose Acetate Coated Charcoals. J. Biomed. Mater. Res. vol. 9, 1975. pp. 143-150.

Viswanathan et al.; Preparation of Biopolymer Fibers by Electrospinning from Room Temperature Ionic Liquids. Biomacromolecules 2006, 7. pp. 415-518.

Elkheshen et al.; Coating charcoal with polyacrylate-polymethacrylate copolymer for haemoperfusion. I: Fabrication and evaluation. J. Microencapsulation, 1992, vol. 9, No. 1. pp. 41-51.

Gang et al.; Quaternized Poly(4-Vinylpyridine) Coated Activated Carbon: Diffusion Controlled Sorption of Chromium (VI). Journal of Environmental Engineering, Aug. 2007. pp. 834-838.

* cited by examiner

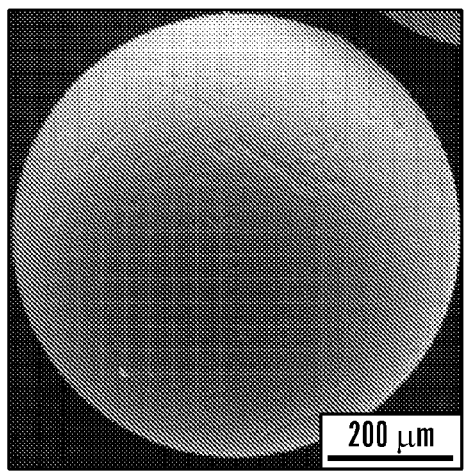
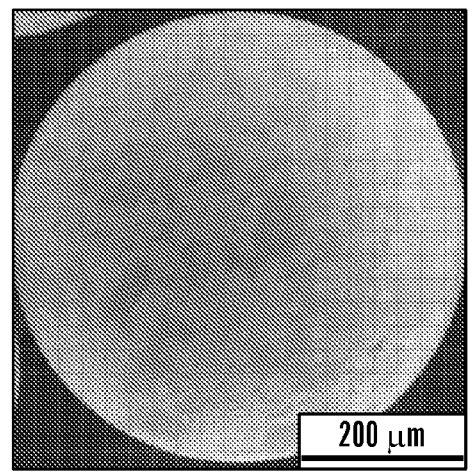
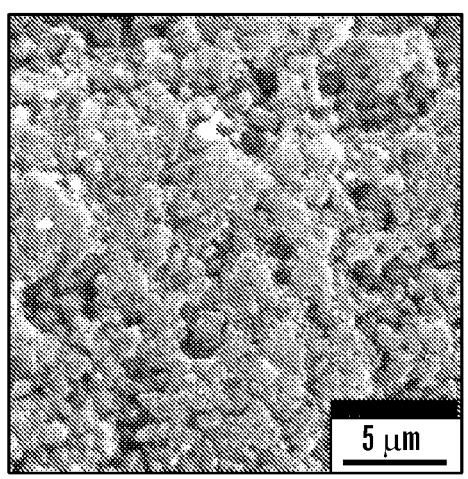
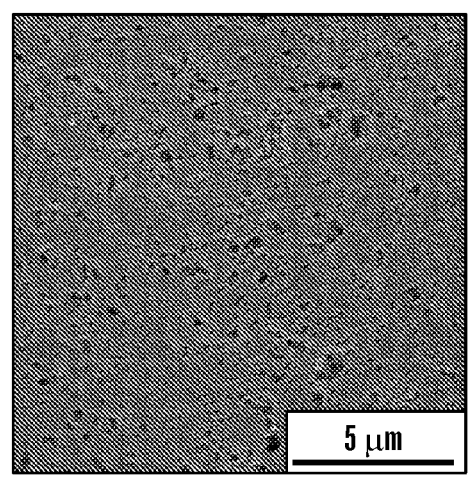
*FIG. 5A* *FIG. 5B*

FILTER COMPOSITES FOR DRUG DETOXIFICATION

RELATED APPLICATION

This present application claims priority to provisional U.S. Patent Application Ser. No. 61/268,626 filed on Jun. 15, 2009.

FIELD OF THE INVENTION

The present invention relates to novel filter composites for drug detoxification,

BACKGROUND OF THE INVENTION

There is a significant medical need for improved treatment of both melanoma and colorectal cancers, particularly when they are metastatic to liver. There are approximately 54,200 new cases of malignant melanoma diagnosed annually in the United States. See Jemal A, Murray T, Samuels A, Ghafoor A, Ward E, Thun M J, Cancer statistics, *CA Cancer J Clin* 53, 5-26, 2003.

Slightly more than 6% of the new cases of malignant melanoma diagnosed annually in the United States are primary ocular melanoma. See Chang A E, Karnell L H, Menck H R., The National Cancer Data Base report on cutaneous and noncutaneous melanoma: a summary of 84,836 cases from the past decade, *Cancer* 83, 1664-1678, 1998.

An estimated 153,760 new cases of colorectal cancer (CRC) were diagnosed in the United States and there were 52,180 deaths from this disease in 2007 (American Cancer Society, Cancer Facts and Figures, 2007).

Unresectable hepatic metastases from solid organ malignancies represent a significant therapeutic challenge in oncology. See Pingpank J F, Libutti S K, Chang R, Wood B J, Neeman Z, Karn A W, Figg W D, Zhai S, Beresneva T, Seidel G D, Alexander H R, Phase I Study of Hepatic Arerial Melphalan Infusion and Hepatic Venous Hemofiltration Using Percutaneously Placed Catheters in Patients with Unsectable Hepatic Malignancies, *J Clin Oncol* 23, 3465-3474, 2005.

For patients with colorectal adenocarcinoma, ocular melanoma, and neuroendocrine tumors, liver metastases frequently represent the sole or predominant site of disease progression. For these patients, systemic and hepatic arterial chemotherapy results in median survivals ranging from 12 to 24 months. See Rothenberg M C, Oza A M, Bigelow R H et al., Superiority of oxaliplatin and fluourouracilleucovorin compared with either therapy alone in patients with progressive colorectal cancer after irinotecan and fluorouracil-leucovorin: Interim results of a phase III trial, *J Clin Oncol* 21, 2059-2069, 2003. See Kemeny N, Gonen M, Sullivan D, et al., Phase I study of hepatic arterial infusion of floxuridine and dexamethasone with systemic irinotecan for unresectable hepatic metastases from colorectal cancer, *J Clin Oncol* 19, 2687-2695, 2001.

For patients with metastatic ocular melanoma who recur, 70% to 90% will develop disease confined to the liver that is multifocal and not amenable to surgical resection. See Egan K M, Seddon J M, Glynn R J, Epidemiologic aspects of uveal melanoma, *Surv Ophthalmol* 32, 239-251, 1988.

Systemic and regional chemotherapy or ablative techniques do not seem to meaningfully impact the natural history of the disease. See Gragoudas E S, Egan K M, Seddon J M., Survival of patients with metastases from uveal melanoma, *Ophthalmology* 98, 383-390, 1991. See Kath R, Hayungs J, Bornfeld N, et al., Prognosis and treatment of disseminated uveal melanoma, *Cancer* 72, 2219-2223, 1993.

Intra-arterial chemotherapy has recently been shown to result in remarkable clinical outcomes because of higher intratumoral concentrations of oncostatics despite minimal adverse effects as compared with those administered systemically. See Eckman W W, Patlak C S, Fenstermacher J D, A critical evaluation of the principles governing the advantages of intra-arterial infusions, *J Pharmacokinetic Biopharm* 2, 257-85, 1974. See Vermorken J B., The role of chemotherapy in squamous cell carcinoma of the uterine cervix: a review, *Int J Gynecol Cancer* 3, 129-142, 1993. See Kusunoki N, Ku Y, Tominaga M, Iwasaki T, Fukumoto T, Muramatsu S, Sugimoto T, Tsuchida S, Takamatsu M, Suzuki Y, Kuroda Y., Effect of sodium thiosulfate on cisplatin removal with complete hepatic venous isolation and extracorporeal charcoal hemoperfusion: a pharmacokinetic evaluation, *Ann Surg Oncol* 8, 449-57, 2001. See Tominaga M, Ku Y, Iwasaki T, Suzuki Y, Kuroda Y, Saitoh Y., Pharmacological evaluation of portal venous isolation and charcoal Hemoperfusion for high-dose intra-arterial chemotherapy of the pancreas, *Br J Sur* 84, 1072-6, 1997. See Jones A and Alexander, Jr. H., Development of isolated Hepatic Perfusion for patients who have unresectable hepatic malignancies, *Surg Oncol Clin N Am* 17, 857-876, 2008.

A higher antitumor effect has generally been accepted to be correlated with higher dose intensity, but is associated with severe toxicity. See Maruo T, Motoyama S, Hamana S, Yoshida S, Ohara N, Yamasaki M, Ku Y., Percutaneous pelvic perfusion with extracorporeal chemofiltration for advanced uterine cervical carcinoma, *Surg Oncol Clin N Am* 17, 843-56, 2008.

The liver has a unique anatomy that provides an opportunity to deliver regional therapy. Established hepatic metastases derive the majority of their blood supply from the hepatic artery, and hepatic arterial infusion of agents with high hepatic clearance during the "first pass" through the hepatic parenchyma allows infusion of high doses of chemotherapy to the diseased organ. See Sigurdson E R, Ridge J A, Daly J M, Fluorodeoxyuridine uptake by human colorectal hepatic metastases after hepatic artery infusion, Surgery, 1986; 100:285-291.

Percutaneous Hepatic Perfusion (PHP), allows physicians to deliver significantly higher doses of anti-cancer drugs to the site of disease without exposing the patient's entire body to those same potent levels of drug. PHP uses a double balloon catheter positioned within the inferior vena cava (IVC) to isolate hepatic venous outflow and divert the blood through an extracorporeal filtration system. Chemotherapy infused through a catheter positioned in the hepatic artery is filtered after the blood exits the liver, so that systemic exposure is limited. The main component of the system is a 16-F, polyethylene double balloon catheter with one large lumen and three accessory lumina. The two low-pressure occlusion balloons are inflated independently. The cephalic balloon blocks the IVC above the hepatic veins, while the caudal balloon obstructs the IVC below the hepatic veins, allowing complete isolation of hepatic venous outflow. The span between the two occlusion balloons consists of a fenestrated segment that feeds into the large central lumen, which exits the catheter from the proximal end. The additional lumen enters the catheter at a point inferior to the caudal balloon and allows some blood flow from the infrarenal IVC to the right atrium. During the procedure, a high dose of a chemotherapeutic agent is infused through a catheter in the hepatic artery. The chemotherapy perfuses the liver and exits the organ through the hepatic veins. Hepatic venous effluent is collected using the double balloon catheter and chemotherapeutic-dosed blood from the central lumen is pumped through an extracorporeal circuit consisting of a centrifugal pump and two activated-carbon filter cartridges arranged in parallel. The filtered blood is returned to systemic circulation via a venous return sheath inserted into the internal jugular vein. Treatments are administered with patients under local or general anesthesia and heparin is administered during the procedure to maintain an ACT of 300 seconds.

The advantages of the PHP approach are that treatment can be delivered without a major operative procedure and that filtration of the hepatic venous effluent can reduce system exposure of cytotoxic chemotherapy by 80% to 90% compared with hepatic artery infusion alone. In clinical trials, 33 patients underwent a total of 77 treatments with dose escalation of doxorubicin from 50 to 120 mg/m$^2$. The systemic exposure of doxorubicin was substantially reduced using hepatic venous hemofiltration. However, because antitumor efficacy was not well established, the technique did not gain widespread application. See Pingpank J F, Libutti S K, Chang R, Wood B J, Neeman Z, Kam A W, Figg W D, Zhai S, Beresneva T, Seidel G D, Alexander H R., Phase I Study of Hepatic Arerial Melphalan Infusion and Hepatic Venous Hemofiltration Using Percutaneously Placed Catheters in Patients with Unsectable Hepatic Malignancies, *J Clin Oncol* 23, 3465-3474, 2005.

Hemoadsorption, or hemoperfusion (HP) as an extracorporeal technique, was introduced in the early 1960s. See Yatzidis H., A convenient hemoperfusion micro-apparatus over charcoal for the treatment of endogenous and exogenous intoxications: Its use as an effective artificial kidney, *Proc Eur Dial Transpl Assoc* 1, 83-87, 1964.

Although the initial results were very successful, this HP procedure induced hypotension, hypocalcaemia, hypokalaemia, hypoglycaemia and thrombocytopenia. See Rosenbaum J L. Poisonings. In Giordano C ed., Sorbents and their clinical applications, New York: Academic Press, 451-67, 1980.

The most severe potential complication from use of the HP technique was the release of fine particles from the carbon granules, causing micro-emboli. See Hagstam K E, Larsson L E, Thysell H., Experimental studies on charcoal hemoperfusion in Phenobarbital intoxication and uremia, including histopathological findings, *Acta Med Scand* 180, 593-610, 1966. See Chang T M., Therapeutic applications of polymeric artificial cells, *Nat Rev Drug Discov.* 4, 221-35, 2005.

The problem of poor biocompatibility of uncoated adsorbents was resolved by coating adsorbent granules with haemocompatible membranes. See Botella J, Ghezzi P M, Sanz-Moreno C., Adsorption in hemodialysis, *Kidney Int Suppl* 76, S60-5, 2000. See Hasirci N, Akovali G., Polymer coating for hemoperfusion over activated charcoal, *J Biomed Mater Res* 20, 963-70, 1986. See el-Kheshen S, Zia H, Badawi A, Needham T E, Luzzi L A., Coating charcoal with polyacrylate-polymethacrylate copolymer for hemoperfusion. III: The effect of the coat thickness on the adsorption capacity of the coated charcoal and its adsorptivity to small and middle size molecules, *J Microencapsul* 12, 505-14, 1995.

Use of coated adsorbents instead of uncoated ones reduces the efficiency of hemoperfusion. As a result, for many years the use of adsorption was limited to only acute poisoning. See Hanasawa K., Extracorporeal treatment for septic patients: new adsorption technologies and their clinical application, *Ther Apher* 6, 290-5, 2002. See Legallais C, Gautier A, Dufresne M, Carpentier B, Baudoin R., The place of adsorption and bio-chromatography in extracorporeal liver support systems, *J Chromatogr B Analyt Technol Biomed Life Sci.* 861, 171-6, 2008. See de Pont A C., Extracorporeal treatment of intoxications, *Curr Opin Crit Care* 13, 668-73, 2007.

Since the 1990s interest in the use of adsorbents in extracorporeal medical devices has been rising again. See Mikhalovsky S V: Emerging technologies in extracorporeal treatment: focus on adsorption, *Perfusion* 18, 47-54, 2003.

By their chemical composition, medical adsorbents can be divided into three major groups: i) activated carbon (AC); ii) synthetic and natural organic polymers; and iii) inorganic adsorbents, such as silica and oxides of titanium and zirconium. Activated carbon is the most powerful adsorbent among all the materials, as it has the largest surface area—in excess of 2000 m$^2$/g and pore volume—up to 1.8 cm$^3$/g. See Bansal R C, Donnet J-B, Stoeckli F., Active carbon, New York, N.Y.: Marcel Dekker, 1988.

In addition to its superior adsorption features, activated carbon has a series of other advantages over other adsorbents in this respect. Firstly, activated carbon is a rigid material that does not swell in water or other solvents, unlike polymers, and does not require special pretreatment in such a solvent. It is also easier to maintain stable flow characteristics of a biological fluid through a column packed with carbon granules than through a column with soft polymer granules. Second, activated carbon is chemically inert compared with polymers, as it does not contain any plasticizer, catalyst or monomer that can leak from the material into the bloodstream. See Mikhalovsky S V: Emerging technologies in extracorporeal treatment: focus on adsorption, *Perfusion* 18, 47-54, 2003.

Use of coated adsorbents instead of uncoated adsorbents dramatically reduces the efficiency of HP, both in terms of adsorption capacity and rate of adsorption. As a result, HP has been limited in use to only acute poisoning with certain low-molecular toxins. See Webb D., Charcoal hemoperfusion in drug intoxication, *Br J Hosp Med* 49, 493-96. 1993.

As many small molecules are protein bound in the blood, they cannot cross the membrane coating. Hence, HP over coated adsorbents would be efficient in removing only protein-free solutes of low molecular mass.

PHP currently utilizes two single-use hemoperfusion cartridges. The filters are arranged in parallel, through which hepatic venous blood passes to remove the chemotherapeutic agent before entering the venous return circuit. Blood flows range from 400 mL/min to 1.2 L/min (combined flows for the two filters in parallel). The filters are packed with a bed of carbon, either in granular or spherical form, which carbon is coated with an agent to improve biocompatibility. Uncoated charcoal would cause significant damage to the blood, including lysis of red blood cells and clotting activation. Uncoated charcoal also tends to be physically unstable, resulting in fine particulates that may enter the blood and pose a safety concern.

Delcath was forced to change filters during the clinical trials when Asahi removed their Hemosorba device from the market. There is only one commercially available activated carbon blood filter available in North America. Gambro markets the Adsorba C filter which utilizes a cylindrical carbon coated with a cellulose matrix. This filter fails to provide high first pass removal of traditional chemotherapeutic agents and is therefore unsuitable for use within the PHP procedure. Delcath is currently using a filter manufactured by Clark Research & Development. The Clark Biocompatible hemoperfusion cartridge was voluntarily removed from commercial distribution, but continues to be used in clinical trials by Delcath under an agreement with the FDA. The Clark filter uses a granular carbon, with a mean grain size in excess of 0.6 mm, which results in the release of fine carbon particles into the blood and lack blood biocompatibility.

Platinum-based drugs are among the most active anticancer agents and have been widely used in the treatment of a variety of human tumors. See Raymond E, Faivre S, Chaney S, Woynarowski J, and Cvitkovic E., Cellular and Molecular Pharmacology of Oxaliplatin, *Mol Cancer Ther* 1, 227-235, 2002.

Over the last 30 years, a large number of platinum analogues has been synthesized to enlarge the spectrum of activity, overcome cellular resistance, and/or reduce the toxicity of both first (e.g., cisplatin) and second generation (e.g., carboplatin) platinum drugs. See Cvitkovic E., A historical perspective on oxaliplatin: rethinking the role of platinum compounds and learning from near misses, *Semin Oncol* 25, 1-3, 1998. See Raymond E, Chaney S G, Taamma A, and Cvitkovic E., Oxaliplatin: a review of preclinical and clinical studies, *Ann Oncol* 9, 1053-1071, 1998. See Raymond E, Faivre S, Woynarowski J M, and Chaney S G., Oxaliplatin: mechanism of action and antineoplastic activity, *Semin Oncol* 25, 4-12, 1998. See Soulie P, Raymond E, Brienza S, and Cvitkovic E., Oxaliplatin: the first DACH platinum in clinical practice, *Bull Cancer* 84, 665-673, 1997. See Cvitkovic E., Ongoing and unsaid on oxaliplatin: the hope, *Br J Cancer* 77 (Suppl. 4), 8-11, 1998.

Oxaliplatin, a diaminocyclohexane-containing platinum, has a spectrum of activity and mechanisms of action and resistance that appear to be different from those of other platinum-containing compounds, notably cisplatin. Oxaliplatin has a cytotoxic effect in a broad range of cell lines, including colon, ovarian, and lung cancer, with $IC_{50}$ values ranging from 0.5 to 240 µM in colon, 0.12 to 19.8 µM in ovarian, and 2.6 to 6.1 µM in lung. See Llory J F, Soulie P, Cvitkovic E, and Misset J L., Feasibility of high-dose platinum delivery with combined carboplatin and oxaliplatin, *J Natl Cancer Inst* (Bethesda), 86, 1098-1099, 1994. See Soulie P, Bensmaine A, Garrino C, Chollet P, Brain E, Fereres M, Jasmin C, Musset M, Misset J L, and Cvitkovic E., Oxaliplatin/cisplatin (L-OHP/CDDP) combination in heavily pretreated ovarian cancer, *Eur J Cancer* 33, 1400-1406, 1997. See Rixe O, Ortuzar W, Alvarez M, Parker R, Reed E, Paull K, and Fojo T., Oxaliplatin, tetraplatin, cisplatin, and carboplatin: spectrum of activity in drug-resistant cell lines and in the cell lines of the National Cancer Institute's Anticancer Drug Screen panel, *Biochem Pharmacol* 52, 1855-1865, 1996. See Pendyala L, Kidani Y, Perez R, Wilkes J, Bernacki R J, and Creaven P J., Cytotoxicity, cellular accumulation and DNA binding of oxaliplatin isomers, *Cancer Lett* 97, 177-184, 1995. See Pendyala L and Creaven P J., In vitro cytotoxicity, protein binding, red blood cell partitioning, and biotransformation of oxaliplatin, *Cancer Res* 53, 5970-5976, 1993. See Holmes J, Stanko J, Varchenko M, Ding H, Madden V J, Bagnell C R, Wyrick S D, and Chaney S G., Comparative neurotoxicity of oxaliplatin, cisplatin, and ormaplatin in a Wistar rat model, *J Toxicol Sci* 46, 342-351, 1998. See Raymond E, Lawrence R, Izbicka E, Faivre S and Von Hoff D D., Activity of oxaliplatin against human tumor colony-forming units, *Clin Cancer Res* 4, 1021-1029, 1998.

In in vivo studies, oxaliplatin is active against breast, colon, and gastric cancer; renal cell carcinoma; and sarcoma. See Pendyala L and Creaven P J., In vitro cytotoxicity, protein binding, red blood cell partitioning, and biotransformation of oxaliplatin, *Cancer Res* 53, 5970-5976, 1993.

In addition, oxaliplatin has been tested in vitro and in vivo against cisplatin-resistant cell lines and tumor models, including human ovarian, lung, cervix, colon, and leukemia cell lines. The filters used are not specific in their removal of aromatic compounds within a broad molecular weight range, but the available validated method of measuring platinum by atomic absorption permits this study to validate the filter removal and blood biocompatibility for oxaliplatin and perhaps other chemotherapeutic agents to be tested.

SUMMARY OF THE INVENTION

The present invention provides a filter, comprising:
  at least one layered structure interior to a bounding surface of the filter;
  wherein each layered structure comprises a carbon structure and a coating on and in direct mechanical contact with a surface of the carbon structure;
  wherein the carbon structure comprises carbon;
  wherein the coating comprises a coating material consisting of cellulose or a methacrylate selected from the group consisting of polymethylmethacrylate (PMMA), polyethylmethacrylate (PEMA), and polyhydroxyethylmethacrylate (PHEMA), and
  wherein the layered structure is configured to remove a contaminant in a flowing liquid as the flowing liquid flows through the filter.

The present invention provides a A filter, comprising:
  at least one layered structure interior to a bounding surface of the filter;
  wherein each layered structure comprises a carbon structure and a coating on and in direct mechanical contact with a surface of the carbon structure;
  wherein the carbon structure comprises carbon;
  wherein the coating comprises a coating material consisting of cellulose or a methacrylate selected from the group consisting of polymethylmethacrylate (PMMA), polyethylmethacrylate (PEMA), and polyhydroxyethylmethacrylate (PHEMA), and
  wherein the layered structure is configured to remove a contaminant in a flowing liquid as the flowing liquid flows through the filter.

The present invention provides a method of forming a suture structure, said method comprising:
  forming a film on a suture that has been previously formed on a mammal,
  wherein the film comprises a coating and a heparin layer,
  wherein the coating is on and in direct mechanical contact with the suture,
  wherein the heparin layer is on and in direct mechanical contact with the coating such that the coating is disposed between the suture and the heparin layer,
  wherein the heparin layer comprises heparin, and
  wherein the coating comprises a coating material consisting of cellulose or a methacrylate selected from the group consisting of polymethylmethacrylate (PMMA), polyethylmethacrylate (PEMA), and polyhydroxyethylmethacrylate (PHEMA).

The present invention provides a filter, comprising:
  a layered structure interior to a bounding surface of the filter;
  wherein the layered structure comprises a charcoal layer, a coating on and in direct mechanical contact with a surface of the charcoal layer, and a heparin layer comprising heparin on and in direct mechanical contact with the coating such that the coating is disposed between the charcoal layer and the heparin layer;
  wherein the coating comprises a coating material consisting of cellulose or polymethylmethacrylate (PMMA), and wherein the layered structure is configured to remove a drug in blood as the blood flows through the filter.

BRIEF DESCRIPTION OF THE DRAWINGS

FIGS. 5A and 5B are field emission scanning electron microscopy (FESEM) images of uncoated charcoal beads and heparin-cellulose-charcoal composites, respectively, in accordance with embodiments of the present invention.

DETAILED DESCRIPTION OF THE INVENTION

Figure 1:
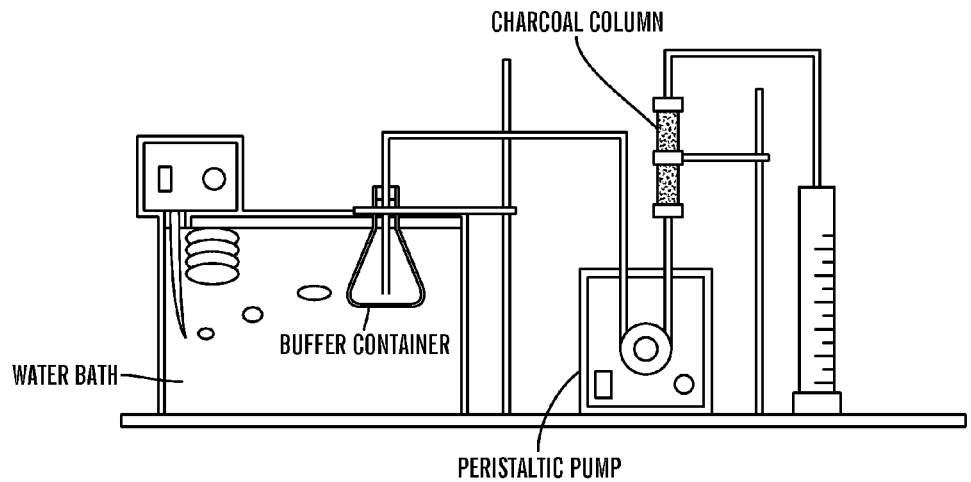
FIG. 1 depicts an apparatus that measures the release of fine charcoal particles.

The present invention provides filters with nanocomposites for the maximum removal chemotherapy such as oxaliplatin and other chemicals from blood while minimizing filter impact on blood chemistry. Initial clinical results from studies treating cancer in the liver using the filter of the present invention confirm that more drug is delivered to the tumor site, and less to the other regions of the body, which enhances tumor shrinkage with improved quality of life over systemic cancer therapies.

The inventive filter has a higher first pass extraction and is blood compatible. The inventive filter comprises a coating, such as a heparinized-methyl methacrylate coating, a heparinized-cellulose coating, and other ocating, to increase first pass extraction while maintaining an environment compatible with whole blood. Novel coating strategies, which are utilized to improve the drug removal efficiency and blood compatibility, include: 1) spray coating; 2) presoaking the charcoal beads with hexane to protect the internal activated surface coating; and 3) using a high viscosity solvent, such as room temperature ionic liquids (RTILs), in the coating process.

Heparin is a common anticoagulant drug used to prevent blood from clotting during surgery and in the treatment of postoperative thrombosis and embolism. See Linhardt R J, Toida T, Heparin oligosaccharides: new analogues-development and applications (Z. J. Witczak and K. A. Nieforth, eds) *Carbohydrates in Drug Design*. Marcel Dekker, NY; p. 277, 1997.

Pharmacologically, heparin is known to catalyze the binding of antithrombin III (ATIII) to thrombin, thus preventing the thrombin-catalyzed conversion of soluble fibrinogen to an insoluble fibrin clot. When blood is exposed to any surface, other than the luminal wall of undamaged vascular endothelium, a process is induced that results in clot formation and complement activation. These reactions protect animals against excessive bleeding and infection. However, they are a source of problems related to the modern clinical application of medical devices made of artificial materials. It has not been possible to prepare specially designed materials that are blood compatible in the absence of heparin. Current devices often require systemic anticoagulation (heparin is given to the patient prior to using the device), thus resulting in the risk of uncontrollable bleeding.

Room temperature ionic liquids, (RTILs) consisting entirely of ionic species, are non-volatile, non-flammable and thermally stable solvents. See Welton T, Room-temperature ionic liquids. Solvents synthesis and catalysis, *Chem Rev* 99, 2071-2083, 1999.

The RTILs have many fascinating properties, which make them of fundamental interest to chemists and chemical engineers. RTILs are liquid range over a large range of temperatures, often ranging from −50° C. to 300° C. The range of physical and chemical properties of RTILs is considerably wider than that of commonly used organic solvents. Thus, appropriate RTILs can be designed with the precise physical and chemical properties desired by the end user. Because RTILs have a very low or a nearly zero vapor pressure, very little RTIL is lost into the environment through evaporation. RTILs are stable to temperatures, and hence, reactions can also be performed in RTILs solvents at elevated temperatures. Some RTILs are water soluble, some are also soluble in conventional organic solvents and some are not. The water solubility of RTILs can be switched on or off, depending on process requirements, by modifying RTIL cation structure or by varying the structure of their anions. RTILs permit quantitative recoveries and multiple reuse affording "green" or environmentally friendly process chemistry.

The dissolution and regeneration of non-derivitized cellulose with RTILs has recently been reported. See Swatloski R P, Spear S K, Holbrey J D, Rogers R D., Dissolution of cellulose with ionic liquids, *J Am Cheml Soc* 124, 4974-4975, 2002.

In preliminary experiments, the inventors of the present invention found that heparin can also be dissolved in RTILs.

Moreover, the inventors of the present invention have been able to cast composite membranes containing cellulose. See Murugesan S, Park T, Yang H, Mousa S and Linhardt R J., Nano-based Neoproteoglycans—Blood Compatible Carbon Nanotubes, *Langmuir* 22, 3461-3463, 2006, See Murugesan S, Mousa S, Vijayaraghavan A, Ajayan P M and Linhardt R J., Ionic Liquid Derived Blood Compatible Composite Membranes For Kidney Dialysis, *J Biomed Mat Res: Part B—App Biomat* 79B, 298-304, 2006;

In addition, the inventors of the present invention have been able to cast composite membranes containing and heparin from RTILs and coating on the activated charcoals. See Park T, Martin J G, Simmons T J, Mousa S, Snezhkova E A, Sarnatskaya V V, Nikolaev V G, Linhardt R J., Biocompatible Activated Charcoal Composites For Drug Detoxification Prepared Using Room Temperature Ionic Liquids, *Chem Commun* submitted, 2008.

The following discussion pertains to research design and methods of the present invention.

The optimal type of filter materials required for maximal removal of oxaliplatin or other chemotherapeutic agents from bovine or human blood is defined. Three different coatings (including cellulose with heparin, PMMA, and PMMA with heparin) may be prepared on spherical charcoal beads and charcoal cylinders as biocompatible blood perfusion charcoal filters.

The charcoal beads are pretreated. Before the coating, charcoal beads are cleaned and washed to remove the fine particles, resulting from mechanical damage during shipping, by washing with saline for five times until the saline wash is clear and colorless. Then the beads are washed with distilled water and dried overnight at 55° C. and heated for 2 hours at 250° C.

Poly(methyl methacrylate) (PMMA) may be used for the coating material. PMMA has excellent biocompatibility with human tissues and has been widely used in various biomedical fields such as intraocular lenses, bone cement in orthopaedics, and injectable biological fluid in cosmetic surgery. To prepare PMMA-charcoal composite, PMMA is dissolved in acetone (10 g/L) under ultrasonic bath at room temperature. The PMMA solution is diluted in different concentrations with acetone. Activated charcoal (5 g) is incubated in 100 mL PMMA solution at 37° C., 100 rpm shaking for different times (1, 2, 3, 5 hours). After the incubation, PMMA coated charcoal is recovered by filtration with 5 μm filter paper. The residual acetone on the charcoal is removed by drying at 80° C. for 5 hours. The weight of charcoal (before and after coating) will be measured to calculate the PMMA content on the coated charcoal.

The PMMA is heparinized by being partially hydrolyzed via treatment with NaOMe/MeOH to afford available carboxyl groups that will be activated with EDC to which heparin will be conjugated through its free amino groups. This conjugation of heparin to PMMA can be accomplished in solution phase and the resultant heparin-PMMA conjugate coated on the charcoal beads or in a two phase system where heparin is conjugated to partially hydrolyzed PMMA previously coated onto charcoal beads.

To prepare heparin-cellulose composites coating in room temperature ionic liquids, cellulose (200 mg, $M_w$=5,800,000) will be added to 10 g of the RTIL, 1-butyl-3-methylimidazolium chloride ([bmIm][Cl]). This mixture is heated at 70° C. for 30 minutes to fully dissolve the cellulose (2% (w/w) cellulose in [bmIm][Cl]). Imidazolium heparin is prepared from pharmaceutical grade heparin as previously described. Imidazolium heparin (100 mg) is added to 10 g of 1-ethyl-3-methylimidazolium benzoate ([emIm][ba]), mixed by vortexing and heated at 35° C. for about 20 min, affording a clear solution (1% (w/w) heparin in [emIm][ba]). The 2% cellulose solution (200 mg in 10 g of [bmIm][Cl]) is combined with an equal volume of 1% heparin in [emIm][ba] and mixed by vortexing for 2 minutes, resulting in a final concentration of 1% (w/w) cellulose and 0.5% (w/w) heparin in [bmIm][Cl]+[emIm][ba]. Uncoated activated charcoal beads (1 g) are added to the heparin-cellulose solution and this mixture is then heated at 50° C. for 2 minutes and mixed by vortexing for 2 minutes to fully coat the charcoal. The resulting suspension is placed in syringes and introduced drop-wise into excess ethanol. The resulting heparin-cellulose coated charcoal beads is washed with ethanol using a rotary shaker (50 rpm) for 24 hours to completely remove the RTILs. Neither cellulose nor heparin are ethanol soluble, thus, the ethanol selectively removes the RTILs from the coated charcoal beads. After removing the ethanol, the charcoal composite is washed with a 16% NaCl solution using a shaker (50 rpm) for 24 hours to convert the imidazolium heparin to sodium heparin and to remove all leachable heparin from the heparin-cellulose coated charcoal beads. Finally, the coated charcoal beads is washed with distilled water using a rotary shaker (50 rpm) for another 3 hours to remove residual sodium chloride and dried in a desiccator.

Strategies to improve the oxaliplatin adsorption efficiency of coated charcoals are as follows. In a study, the inventors of the present invention found that oxaliplatin adsorption efficiency was decreased on coating with PMMA. A thick coating of PMMA on the charcoal bead reduces oxaliplatin adsorption efficiency. To optimize the coating, different concentration of PMMA and reduced incubation time may be tested. The reduced adsorption efficiency may also be due to the coating of the internal activated surface in the charcoal. To address this issue, three different strategies may be applied: 1) spray coating; 2) presoaking the charcoal beads with hexane to protect the internal activated surface coating and then removing the hexane by drying; and 3) using high viscosity solvent, such as RTIL, in the coating process.

A study may be conducted to evaluate the efficiency of adsorption of oxaliplatin with different coated charcoal beads. In this study, a 100 μg/mL solution of oxaliplatin in bovine blood may be prepared by dissolving about 500 μg oxaliplatin in 100 μL of a 5% dextrose solution, and adding and mixing it with 4.9 mL of fresh bovine blood. The solution may be transferred to a 20 mL vial containing 250 mg coated charcoal and mixed on a rotatory shaker for 30 minutes. The solution may then be filtered using Whatman No. 1 filter paper. Plasma may be separated by centrifugation and oxaliplatin concentration may be measured by AA spectroscopy using a previously validated analytical method developed for quantification of oxaliplatin in plasma.

Fine particulates entering the blood may pose a safety concern. FIG. 1 depicts an apparatus that measures the release of fine charcoal particles. See el-Kheshen S, Zia H, Badawi A, Needham T E, Luzzi L A., Coating charcoal with polyacrylate-polymethacrylate copolymer for hemoperfusion. III: The effect of the coat thickness on the adsorption capacity of the coated charcoal and its adsorptivity to small and middle size molecules, *J Microencapsul* 12, 505-14, 1995.

In FIG. 1, 100 ml of filtered (Millipore 0.45 μM) phosphate buffer solution pH 7.4 will be equilibrate in a water bath at 37° C. for 30 min. The buffer is bumped with a peristaltic pump through a column packed with 2 g of different coated charcoal. The column may be made of glass, 10 cm length and 1.5 cm diameter and with a 100 μm frit fixed on each end. The buffer may be pumped against gravity, collected at the distal end, filtered again through a Millipore filter of 0.45 μm pore size. The fine particles trapped on this filter will be counted on a light microscope.

The effects of charcoal on blood coagulation parameters may be evaluated by measuring levels of heparin and fibrinogen in the blood at predefined points after mixing with charcoal. Bovine blood (5 mL) may be added to a 20 mL vial containing 250 mg of the charcoal material to be tested. The test vial may be mixed on a rotatory shaker for 60 minutes. Samples (0.5 mL) may be withdrawn at 15, 30, and 60 minutes for measurement of fibrinogen. At the end of the experiment, the contents of the vial is filtered using Whatman No. 4 filter paper. Heparin levels are measured in the filtrate. Plasma may be obtained by centrifuging the samples at 3000 rpm for 10 minutes, and fibrinogen may be measured on an ACL-8000 coagulation analyzer (Beckman Coulter). Calibration standards and controls may be purchased from Beckman Coulter. Results may be compared to fibrinogen levels measured in plasma obtained from bovine blood without charcoal.

Heparin may be isolated from plasma and measured by the carbazole assay. Plasma samples (2 mL) may be individually subjected to proteolysis at 55° C. with 10% of Actinase E (20 mg/mL) for 18 h. After the proteolysis, dry urea and dry CHAPS may be added to each sample (2 wt % in CHAPS and 8 M in urea). The resulting solutions are clarified by passing through a syringe filter containing a 0.2 μm membrane. A Vivapure MAXI Q M spin column (Viva Science) is equilibrated with 3 mL of 8 M urea containing 2% CHAPS (pH 8.3). The clarified filtered samples are loaded and run through the spin columns under centrifugal force (500×g). The columns are first washed with 3 ml of 8 M urea containing 2% CHAPS at pH 8.3, and then washed three times with 5 mL of 200 mM NaCl. Heparin will be released from the spin column by washing 3-times with 1 mL of 16% NaCl. To quantify the amount of heparin in each sample using heparin as a standard, heparin will be recovered with methanol precipitation and be subjected to carbazole assay. See Bitter T and Muir H M., A modified uronic acid carbazole reaction, *Anal Biochem* 4, 330-334, 1962.

The effects of charcoal on blood cells may be assessed by gently mixing a small amount of human blood (2 mL) with around 100 mg of charcoal for 30 minutes. 200 μL samples are drawn after 15 minutes and after 30 minutes. The samples may be measured directly in a hematology Coulter Counter (AcT Diff2). Results may be compared to blood counts taken at the same time points from a blank with no charcoal.

ATP secretion from platelets is one of the parameters used to describe platelet functionality and survival. ATP secretion along with platelet aggregation in samples of platelet-rich plasma may be measured in a Chrono-log Lumi-Aggregometer (Model 700). Samples may be prepared by gently mixing 25 mL of bovine blood with 1.25 g of coated or uncoated charcoal on a rotator for 30 minutes. Samples may be then centrifuged following the established protocol to prepare platelet-rich plasma and platelet-poor plasma for analysis of aggregation and ATP secretion. The results may be compared to aggregation and ATP secretion results in charcoal-free samples mixed on a rotatory shaker for 30 minutes. The study may be repeated replacing bovine blood with human blood.

An optimized coating procedure may be scaled up to 500 mL. A small portion of this batch may be assessed and the coated beads may be analyzed for coating thickness and porosity using SEM. See Murugesan S, Mousa S, Vijayaraghavan A, Ajayan P M and Linhardt R J., Ionic Liquid Derived Blood Compatible Composite Membranes For Kidney Dialysis, *J Biomed Mat Res: Part B—App Biomat* 79B, 298-304, 2006.

The optimal coated charcoal may be packed onto the filter column (in 6 cm diameter and 19 cm long). Oxaliplatin removal from heparinized bovine blood may be performed using an initial drug concentration of 100 mg/L. The perfusion system may be set up with the column as shown in a preliminary study (see FIG. 2, discussed infra). The filter may be primed with 2 L of a 5% dextrose solution at 1000 mL/min. The oxaliplatin solution may be pumped through the filter system at 500 mL/min. The samples may be collected from the pre-filter sampling port at 0, 1, 5, 10, 20, and 30 minutes following pumping of the oxaliplatin solution, and from the post-filter sampling port at 1, 5, 10, 20 and 30 minutes. The reservoir may be also sampled after 30 minutes. The concentrations of oxaliplatin in these samples may be analyzed by AA Spectroscopy. Blood heparin levels, coagulation parameters, platelet activation state and hematocrit may be monitored.

Figure 2:
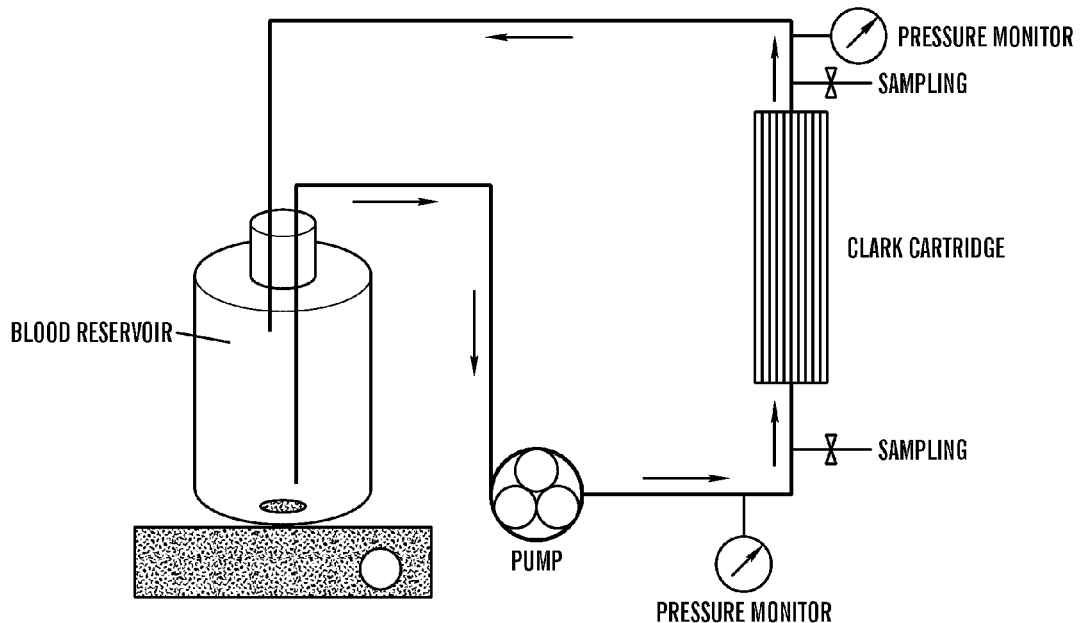
FIG. 2 depicts a perfusion system for testing the efficiency of the Clark Biocompatible Hemoperfusion Charcoal Filter for removing oxaliplatin, in accordance with embodiments of the present invention.

FIG. 2 depicts a perfusion system for testing the efficiency of the Clark Biocompatible Hemoperfusion Charcoal Filter for removing oxaliplatin, in accordance with embodiments of the present invention. Examination of oxaliplatin (at 100 mg/L) removal from 5% dextrose and bovine blood was performed and discussed infra in conjunction with FIGS. 3A and 3B. The perfusion system was set up with the Clark filter as shown in FIG. 2. The perfusing fluid (5% dextrose or bovine blood) was stirred at medium speed during the experiment. The filter was primed with around 2 L of a 5% dextrose solution at 1000 mL/min. The oxaliplatin solution was pumped into the system at 500 mL/min. The samples were collected from the pre-filter sampling port at 0, 1, 5, 10, 20, and 30 minutes following pumping of the oxaliplatin solution, and from the post-filter sampling port at 1, 5, 10, 20 and 30 minutes. The reservoir was also sampled using a graduated pipette after 30 minutes.

The concentrations of oxaliplatin in these samples were subject to analysis using Atomic Absorption Spectroscopy (AA). See Hull D A, Muhammad N, Lanese J G, Reich S D, Finkelstein T T, Fandrich S., Determination of platinum in serum and ultra-filtrate by flameless atomic absorption spectrophotometry, *J Pharm Sci* 70, 500-2, 1981.

Figure 3A:
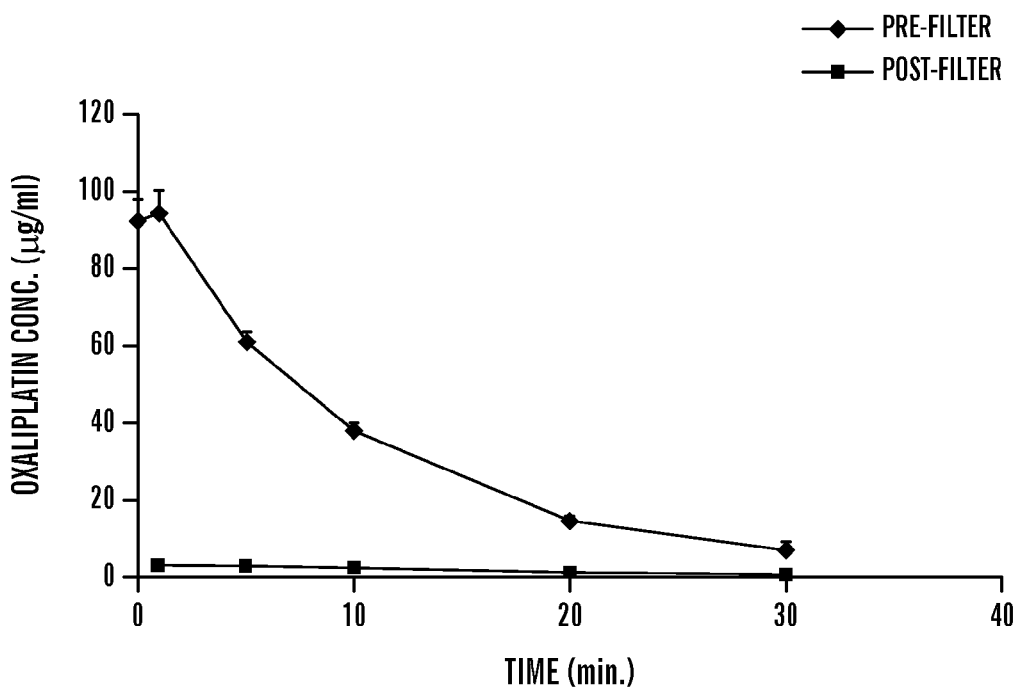
FIGS. 3A and 3B depict plots of oxaliplatin concentration versus time in 5% dextrose and bovine blood respectively, from use of the perfusion system of FIG. 2 for removal of the oxaliplatin from 5% dextrose and bovine blood, in accordance with embodiments of the present invention.
Figure 3B:
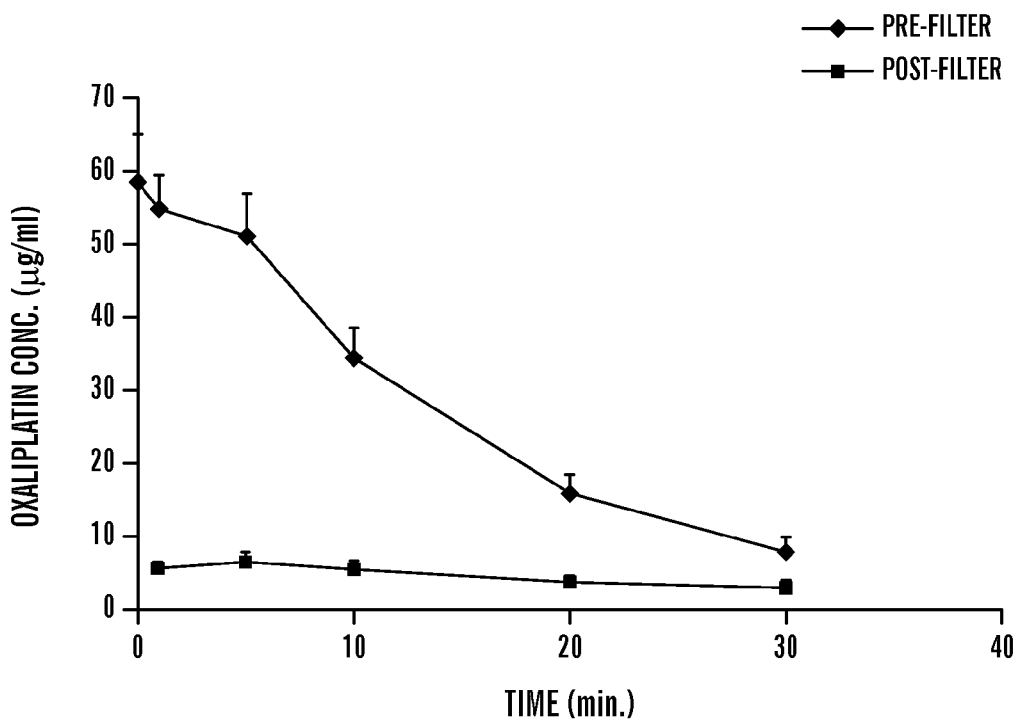

FIGS. 3A and 3B depict plots of oxaliplatin concentration versus time in 5% dextrose and bovine blood respectively, from use of the perfusion system of FIG. 2 for removal of the oxaliplatin from 5% dextrose and bovine blood, in accordance with embodiments of the present invention. The results in FIGS. 3A and 3B from the average of the three runs for 5% dextrose and bovine blood shows that the filters were effective in removing oxaliplatin from the circulating fluid, with average percent removal ratios of 93.4% and 92.3% from dextrose solution and bovine blood, respectively. However, it was observed that the filters released substantial amounts of fine carbon particulates in this preliminary study, even though the charcoal had been coated with 2-hydroxymethyl methacrylate.

Figure 4A:
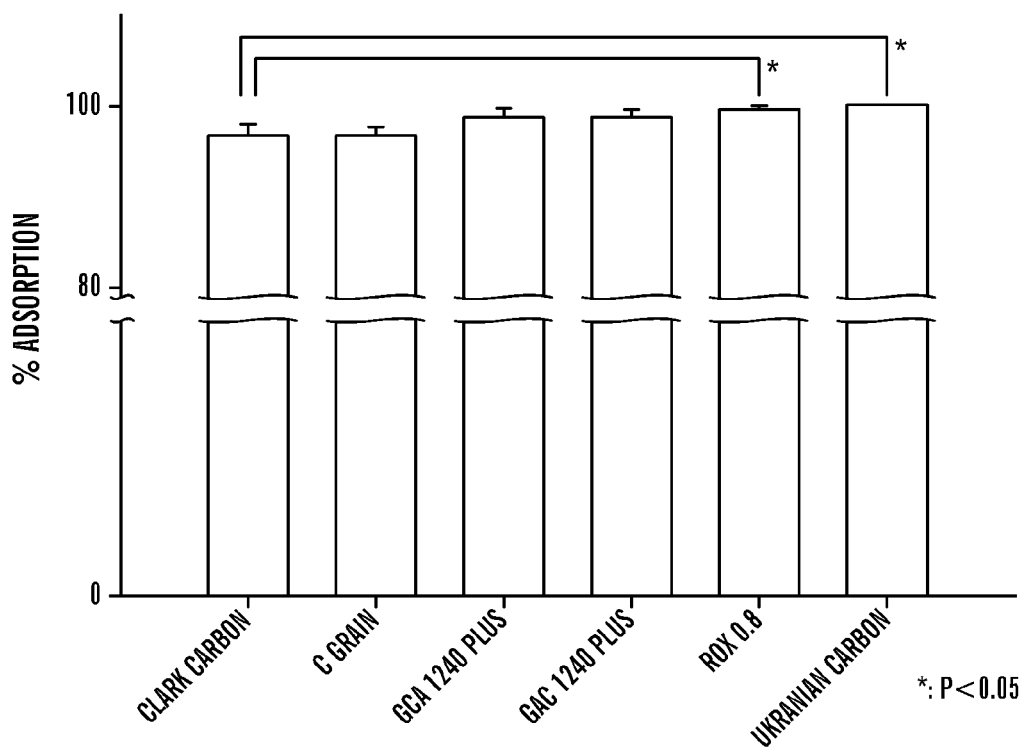
FIG. 4A depicts the results of an evaluation of the efficiency of adsorption of oxaliplatin in 5% dextrose directly with uncoated charcoals from different suppliers, in accordance with embodiments of the present invention.

FIG. 4A depicts the results of an evaluation of the efficiency of adsorption of oxaliplatin in 5% dextrose directly with uncoated charcoals from different suppliers, in accordance with embodiments of the present invention. The results in FIG. 4A show that all the adsorption efficiency of uncoated charcoals was high (ranging from 97.0% to 99.7%). Ukrainian carbon (spherical beads of 1.5 mm diameter) provides the highest adsorption efficiency in FIG. 4A. Unlike the granular charcoal used in the Clark filter, the Ukrainian spherical charcoal beads are less fragile and do not produce fines.

Figure 4B:
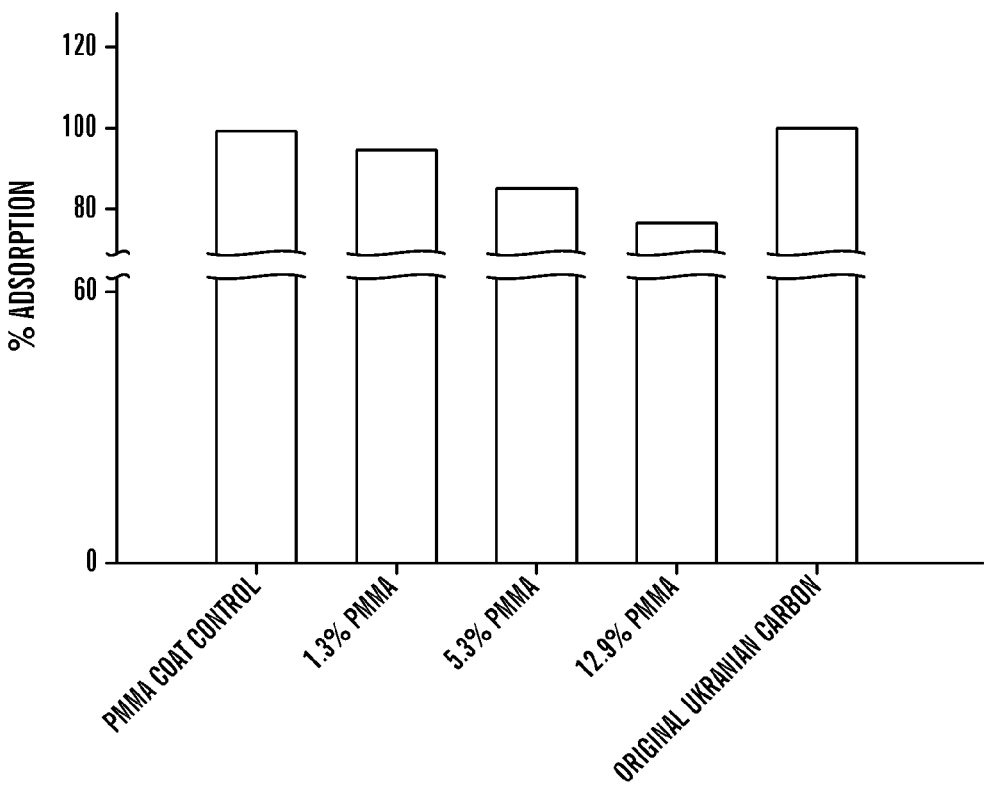
FIG. 4B depicts the results of an evaluation of the efficiency of adsorption of oxaliplatin in 5% dextrose directly with Ukrainian carbon spherical beads of 1.5 mm diameter coated with different amounts of PMMA, in accordance with embodiments of the present invention.

FIG. 4B depicts the results of an evaluation of the efficiency of adsorption of oxaliplatin in 5% dextrose directly with Ukrainian carbon spherical beads of 1.5 mm diameter coated with different amounts of PMMA, in accordance with embodiments of the present invention. FIG. 4B shows that the oxaliplatin adsorption efficiency decreases as the PMMA coating thickness increases.

Activated charcoal is useful for treating individuals in danger from oral drug overdose of depressants such as alcohol, barbiturates, and benzodiazepines, or stimulants such as ecstasy, cocaine, amphetamines. See T. Nakamura, Y. Oida, K. Matsumoto, N. Kawasaki, and S. Tanada, *J. Environ. Sci. Healt, A. Tox. Hazard. Subst. Environ. Eng.*, 2002, 37, 905-912. See M. Melillo, G. J. Phillips, J. G. Davies, A. W. Lloyd, S. R. Tennison, O. P. Kozynchenko, and S. V. Mikhalovsky, *Carbon*, 2004, 42, 565-571.

However, uncoated activated charcoal generally results in thromboresistance when used in direct hemoperfusion to such an extent that modified cellulose-charcoal composites have been used for drug detoxification, since the first literature of cellulose coating of charcoal was shown in 1975. See V. V. Sarnatskaya, W. E. Lindup, P. Walther, V. N. Maslenny, L. A. Yushko, A. S. Sidorenko, A. V. Nikolaev, and V. G. Nikolaev, *Artif. Cell. Blood. Sub.*, 2002, 30, 113-126. See L. K. Mathur, J. M. Jaffe, J. L. Colaizzi, and R. W. Moriarty, *Am. J. Hosp. Pharm.*, 1976, 33, 717-719. See P. Crome, G. Hampel, B. Widdop, and R. Goulding, *Postgrad, Med. J.*, 1980, 56, 763-766. See R. G. Peterson, and L. N. Peterson, *Pediatr. Clin. North. Am.*, 1986, 33, 675-689. See J. F. Winchester, and C. D. Ronco, *Adv. Ren. Replace. Ther.*, 2002, 9, 19-25. See E. Denti, M. P. Luboz, and V. Tessore, *J. Biomed. Mater. Res.*, 1975, 9, 143-150.

Unfortunately, the use of cellulose-charcoal composites in hemoperfusion still requires such additional measures as whole blood citratization and the addition of human serum albumin due to the lack of blood compatability with cellulose-charcoal composites.

To address this problem, the inventors of the present invention prepared novel biocompatible and blood compatible heparin-cellulose-activated charcoal bead composites using room temperature ionic liquids (RTILs) to enhance the biocompatibility and blood compatibility of activated charcoal beads while decreasing the size of their active pores. This coating decreases the active pore size of the activated charcoal, thus, diminishing its rate of protein adsorption, without decreasing the effective removal of free-diluted and protein-bound small drug molecules. These composites are useful for the rapid and safe removal of small, hydrophobic protein-bound drug molecules from the digestive system or from the blood of overdose patients in an extracorporeal circuit. A model system for blood detoxification, containing biocompatible and blood compatible charcoal composites, is examined using the hydrophobic small molecule, phenytoin, and the large protein molecule, bovine serum albumin (BSA).

Cellulose (20 mg, $M_w$=5,800,000) was added to 1 g of the RTIL, 1-butyl-3-methylimidazolium chloride ([bmIm][Cl]). This mixture was then heated at 70° C. for 30 minutes to fully dissolve the cellulose (2% (w/w) cellulose in [bmIm][Cl]).

Imidazolium heparin was prepared from pharmaceutical grade heparin as previously described. See R. P. Swatloski, S. K. Spear, J. D. Holbrey, and R. D. Rogers, *J. Am. Chem. Soc.*, 2002, 124, 4974-4975; (2) G. Viswanathan, S. Murugesan, V. Pushparaj, O. Nalamasu, P. M. Ajayan, and R. J. Linhardt, *Biomacromolecules*, 2006, 7, 415-418.

Imidazolium heparin (10 mg) was added to 1 g of 1-ethyl-3-methylimidazolium benzoate ([emIm][ba]), mixed by vortexing and heated at 35° C. for about 20 min, affording a clear solution (1% (w/w) heparin in [emIm][ba]). The 2% cellulose solution (20 mg in 1 g of [bmIm][Cl]) was combined with an equal volume of 1% heparin in [emIm][ba] and mixed by vortexing for 2 min, resulting in a final concentration of 1% (w/w) cellulose and 0.5% (w/w) heparin in [bmIm][Cl]+[emIm][ba]. Uncoated activated charcoal beads (100 mg, prepared from resin pyrolysis) were added to the heparin-cellulose solution and this mixture was then heated at 50° C. for 2 minutes and mixed by vortexing for 2 minutes to fully coat the charcoal. The resulting suspension was placed in syringes and introduced drop-wise into excess ethanol. The resulting heparin-cellulose coated charcoal beads were washed with ethanol using a rotary shaker (50 rpm) for 24 hours to completely remove the RTILs. Neither cellulose nor heparin are ethanol soluble. Thus, the ethanol selectively removes the RTILs from the coated charcoal beads. After removing the ethanol, the charcoal composite was washed with a 16% NaCl solution using a shaker (50 rpm) for 24 hours to convert the imidazolium heparin to sodium heparin and to remove all leachable heparin from the heparin-cellulose coated charcoal beads. Finally, the coated charcoal beads were washed with double distilled water using a rotary shaker (50 rpm) for another 3 hours to remove residual sodium chloride. The heparin-cellulose coated charcoal bead composite was recovered from the water and dried in a desiccator.

The weight of 500 uncoated charcoal beads (bulk density, $\gamma$=0.20 g/mL) was determined to be 14.6 mg, and 500 heparin-cellulose charcoal beads ($\gamma$=0.23 g/mL) weighed 21.9 mg. Thus, 5 mg charcoal preparation contained 5 mg uncoated charcoal beads, and 7.5 mg heparin-cellulose-charcoal (HCC) composites contained 2.5 mg heparin-cellulose on 5 mg of uncoated charcoal beads (50% of the weight of the uncoated charcoal).

Charcoal beads can typically be coated with polymers at ~10 wt. %. See S. Elkheshen, H. Zia, T. E. Needham, A. Badawy, and L. A. Luzzi, *J. Microencapsul.*, 1992, 9, 41-51.

Recently, 30 wt. % coatings of poly(4-vinylpyridine) on activated charcoal have been reported. See D. Gang, R. K. Kadari, and B. Deng, *J. Envir. Engrg.*, 2007, 133, 834-838.

Thus, it was unexpected that highly viscous RTILs could afford cellulose-heparin coatings of 50 wt. % on charcoal that preserved the original adsorption characteristics of uncoated charcoal.

Field emission scanning electron microscopy (FESEM) was used for the surface characterization of both uncoated charcoal beads and heparin-cellulose-charcoal composites (see FIGS. 5A and 5B, discussed infra) in conjunction with a new approach by the present invention for coating activated charcoal to reduce its surface porosity to large molecules. FESEM clearly shows a decrease in the surface pore size in the coated charcoal preparations, which results in decreased protein adsorption while maintaining the bulk material's ability to adsorb small drug molecules. These biocompatible and blood compatible charcoal composites might be useful for direct hemoperfusion to remove free-diluted and protein-bound toxins of small size or useful as potential oral agents in the cases when strict preservation of large molecules, proteins, is necessary. This successful development of novel heparin-cellulose-charcoal composites still requires in vivo evaluation, which the inventors of the present invention plan to perform in rabbits.

Using Ukrainian charcoal, novel biocompatible and blood compatible heparin-cellulose-activated charcoal bead composites were prepared using room temperature ionic liquids (RTILs). This coating decreases the active pore size of the activated charcoal, thus, diminishing its rate of protein adsorption, without decreasing the effective removal of free-diluted and protein-bound small drug molecules. These composites are useful for the rapid and safe removal of small, hydrophobic protein-bound drug molecules from the digestive system or from the blood of overdose patients in an extracorporeal circuit. In the initial studies conducted by the inventors of the present invention, a model system for blood detoxification, containing biocompatible and blood compatible charcoal composites, was examined using the hydrophobic small molecule, phenytoin, and the large protein molecule, bovine serum albumin (BSA).

FIGS. 5A and 5B are field emission scanning electron microscopy (FESEM) images of uncoated charcoal beads and heparin-cellulose-charcoal composites, respectively, in accordance with embodiments of the present invention. The heparin-cellulose-charcoal charcoal composites were successfully prepared using RTILs.

The FESEM images in FIGS. 5A and 5B depict a surface characterization of the uncoated charcoal beads and heparin-cellulose-charcoal composites, respectively. The FESEM image of uncoated charcoal beads (FIG. 5A) shows a rough, highly porous structure with large, multi-micron-sized pores both capable of allowing the penetration of large proteins and small drug molecules. The FESEM image of heparin-cellulose-charcoal composites (FIG. 5B) shows the smooth, uniformly coated surface with a large number of small, nano-sized pores, potentially capable of inhibiting the adsorption of proteins while permitting small drug molecules to adsorb to the underlying charcoal bead.

Activated partial thromboplastin time (APTT), used in evaluating the blood compatibility of heparinized polymer surfaces, was carried out to measure anticoagulant activity of heparin-cellulose-charcoal composites in human plasma. The plasma did not clot over the course of 1 hour, when exposed to 7.5 mg (2.5 mg heparin-cellulose on 5 mg uncoated charcoal) of heparin-cellulose-charcoal composite, giving no measurable APTT. To obtain measurable APTT for heparin-cellulose-charcoal composite, 3 mg (1 mg heparin-cellulose on 2 mg uncoated charcoal) of sample was used to afford an APTT value of 79.9±2.5 s. This compares favorably to 2 mg of uncoated charcoal bead APTT value of 50.4±0.9 s. Thus, heparin-cellulose-charcoal composites clearly offer the excellent blood-compatibility characteristics, which should prove useful in the application of these heparin-cellulose-charcoal composites in extracorporeal blood detoxification.

The concentration of non-adsorbed (soluble) BSA was measured using the Pierce BCA Protein Assay and the concentration of non-adsorbed (soluble) phenytoin was measured by UV absorbance at 230 nm. (A) each 5 mg charcoal preparation was shaken (70 rpm) in 1 ml phenytoin stock solution (20 mg/mL at pH 6.3) at room temperature. (B) Each 5 mg charcoal preparation was shaken (70 rpm) at room temperature in different concentrations of 1 ml BSA stock solution (5, 50, 100, 500, and 1000 mg/mL at pH 6.3) until equilibrium is reached (24 h).

Figure 6A:
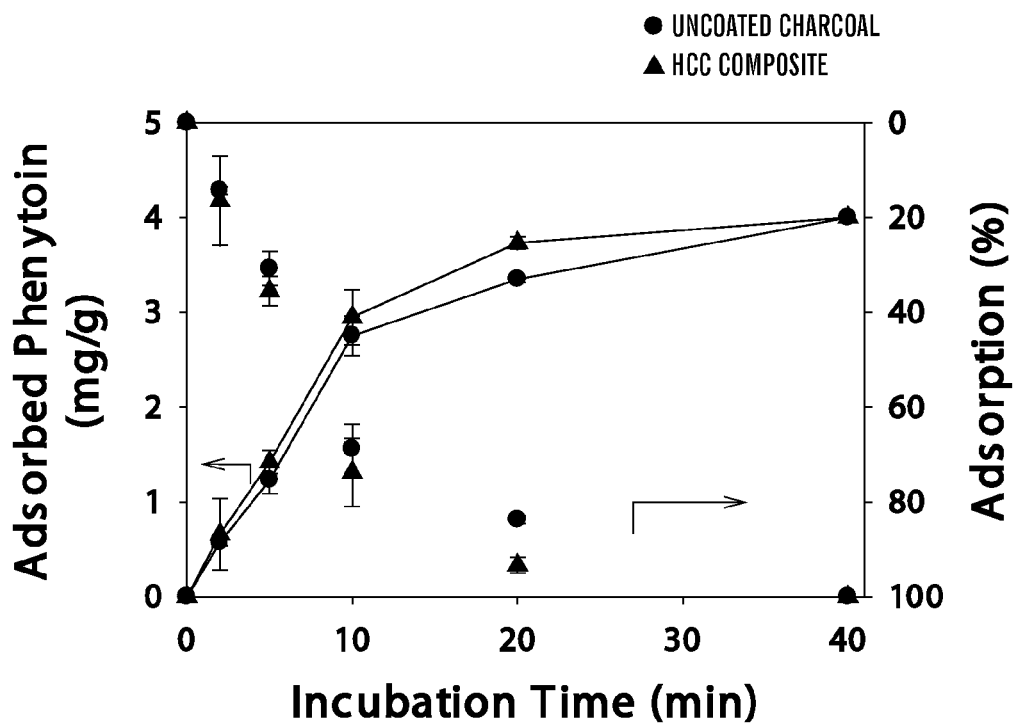
FIG. 6A is a plot of phenytoin adsorption versus time for uncoated charcoal and heparin-cellulose-charcoal (HCC) composites, in accordance with embodiments of the present invention.

FIG. 6A is a plot of phenytoin (5,5-diphenylhydantoin sodium, $M_w$ 274.3) adsorption versus time for uncoated charcoal and heparin-cellulose-charcoal (HCC) composites, in accordance with embodiments of the present invention. The concentration of non-adsorbed (soluble) phenytoin was measured by UV absorbance at 230 nm. Each 5 mg charcoal preparation was shaken (70 rpm) in 1 ml phenytoin stock solution (20 mg/mL at pH 6.3) at room temperature.

Figure 6B:
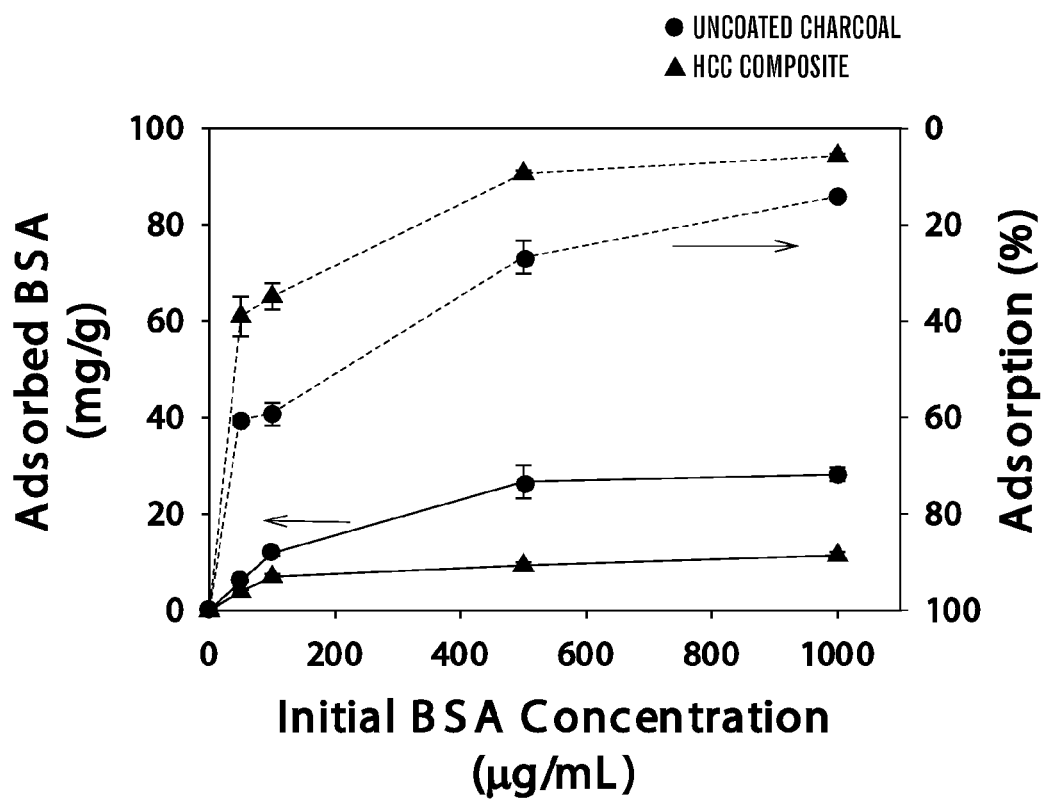
FIG. 6B is a plot of BSA adsorption versus initial BSA concentration for uncoated charcoal and heparin-cellulose-charcoal (HCC) composites, in accordance with embodiments of the present invention.

FIG. 6B is a plot of BSA ($M_w$ 66,430) adsorption versus initial BSA concentration for uncoated charcoal and heparin-cellulose-charcoal (HCC) composites, in accordance with embodiments of the present invention. The concentration of non-adsorbed (soluble) BSA was measured using the Pierce BCA Protein Assay. Each 5 mg charcoal preparation was shaken (70 rpm) at room temperature in different concentrations of 1 ml BSA stock solution (5, 50, 100, 500, and 1000 mg/mL at pH 6.3) until equilibrium is reached (24 hours). The heparin-cellulose-charcoal (HCC) composites showed reduced BSA adsorption compared to uncoated charcoal beads, while retaining the same ability to adsorb phenytoin. Since both uncoated charcoal beads and heparin-cellulose-charcoal composites removed 100% of the phenytoin within a period of 1 hour, the capacity of phenytoin adsorbed onto the heparin-cellulose-charcoal composite was similar to uncoated charcoal beads. The heparin-cellulose-charcoal (HCC) composites resulted in a 9% decrease in BSA from 500 μg BSA in 1 mL stock solution after 24 h, while the uncoated charcoal composites resulted in a 27% decrease in BSA.

Thus, spherical carbon beads are a stable, non-friable matrix capable of removing 97-99% of oxaliplatin from 5% dextrose solution. Coating these spherical particles with a cellulose-heparin composite nanoporous membrane allows the selective adsorption of small hydrophobic molecules, phenytoin, with reduced loss of blood protein (albumin) and without activation of the blood coagulation cascade. The irregular shape of the granulated charcoal used in the Clark filter appears to have given rise to fines and that activated charcoal with either a spherical or possibly cylindrical shape would be optimal for particle stability. Furthermore, a coating, either PMMA or cellulose will decrease damage to formed blood components including red blood cells, while blood cells and platelets decrease protein adorption. This coating should be nanoporous and localized to the outer surface of the carbon beads. The heparin in the bead coating reduces activation of the coagulation cascade and reduces the required level of systemic heparinizatin on PHP.

Figure 7:
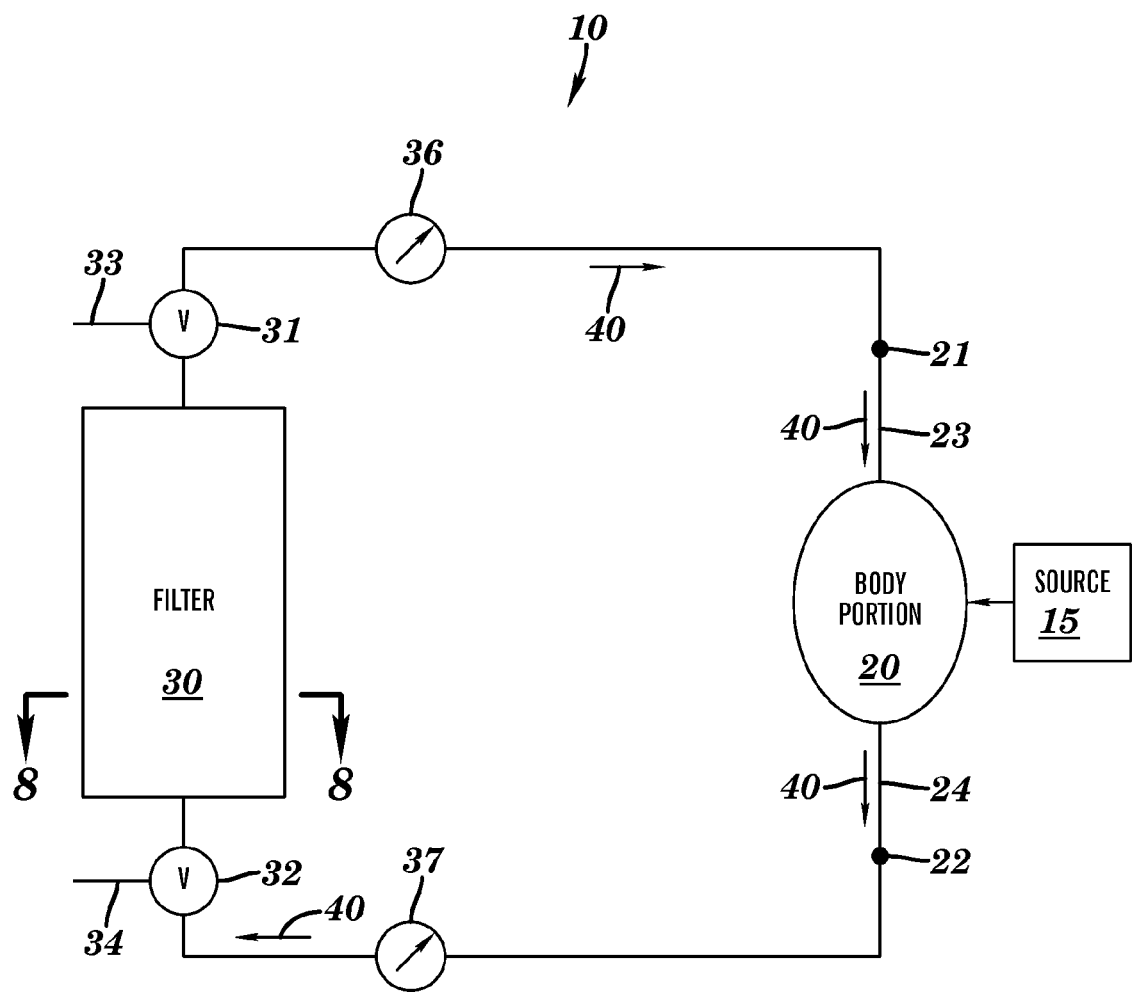
FIG. 7 depicts a filtration system comprising a filter, in accordance with embodiments of the present invention.

FIG. 7 depicts a filtration system 10 comprising a filter 30, in accordance with embodiments of the present invention. The filtration system 10 comprises the filter 30, valves 31 and 32, sampling lines 33 and 34, and pressure gauges 36 and 37. The filtration system 10 is connected to a mammal at connection points 21 and 22 of the mammal. The mammal, which may be a human being or a non-human mammal (e.g., a dog, a horse, etc.), comprises a body portion 20 through which a biological fluid (e.g., blood) of the mammal is circulated by the mammal's heart (not shown) functioning as a pump for circulating blood through the mammals blood circulatory system as well as through the filtration system 10. The biological fluid exits the body of the mammal by entering the filtration system at point 22, then passes through the filter 30, and then re-enters the body of the mammal at point 21. For example, the blood, after passing into a blood vessel 24 (e.g., a vein) from the body portion, exits the body of the mammal by entering the filtration system at point 22 on the vein, then passes through the filter 30, and then re-enters the body of the mammal at point 21 into a blood vessel 23 (e.g., an artery).

The filter 30 removes a contaminant from the blood of the mammal in an efficient and safe manner due to the composition of the filter 30. The contaminant may comprise an unwanted chemical, a pharmaceutical drug (e.g., a chemotherapy drug or any other drug), a toxin, a poison, a virus, alcohol, etc. The biological fluid (e.g., blood) circulates through the filtration system 10 and the body portion 20 directionally as shown by direction arrows 40.

In one embodiment, the body portion 20 is an organ (e.g., liver, pancreas, kidney, lung) being treated by a drug obtained by the organ from a source 13 via an established medical procedure (intravenous drip, hypodermic needle, catheter, etc.). For example, the organ may be treated for cancer (e.g., liver cancer) by chemotherapy in which the chemotherapy drug of the chemotherapy, which is directed into the organ 20 from the source 13, is removed from the blood by the filter 30. Generally, the organ 20 may be treated by a drug or a plurality of drugs received from the source 13 for any disease, wherein the filter 30 is configured to remove the drug(s) from the blood efficiently and safely due to the composition of the filter 30.

In one embodiment, the body portion 20 is the blood circulatory system of the mammal, wherein toxins, chemicals, drugs and/or other contaminants in the blood circulating in the blood circulatory system are removed from the blood by the filter 30. For example, the mammal may be treated by renal dialysis to remove metabolic wastes from the blood because a failing/failed kidney of the mammal is unable to effectively remove metabolic wastes from the blood, wherein the filtration system 10 comprising the filter 30 is incorporated within the dialysis apparatus to assist removal of the metabolic wastes (as well as other toxins and impurities) from the blood. As another example, the mammal may have a toxic overdose of alcohol, a toxin, a poison, etc. in the blood, wherein the filter 30 serves to rapidly and safely remove the alcohol, toxin, poison, etc. from the circulating blood of the mammal, and may be useful in a medical facility such as an urgent care center or an emergency room of a hospital.

The valves 31 and 32 may be closed to disconnect the filtration system 10 from the body portion 20, or may be open to connect the filtration system 10 to the body portion 20.

The sampling lines 33 and 34 are connected to the valves 31 and 32, respectively, and may be used to obtain blood samples when the valves 31 and 32 are opened.

The pressure gauges 36 and 37 may be used to measure the pressure of the blood (or other biological fluid being processed by the filter apparatus 10) at the respective locations of the pressure gauges 36 and 37.

Figure 8:
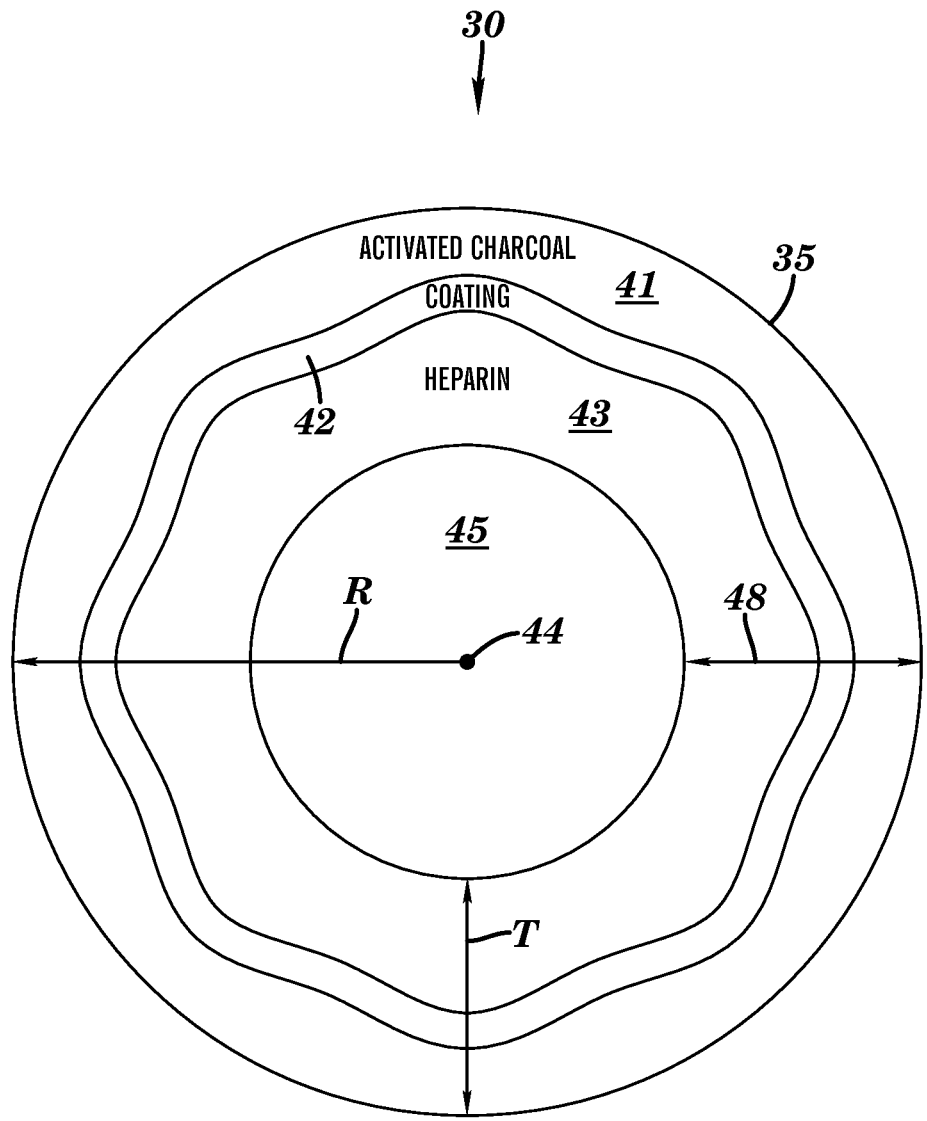
FIG. 8 is a cross-section view through line 8-8 of the filter of FIG. 7, in accordance with embodiments of the present invention.

FIG. 8 is a cross-section view through line 8-8 of the filter 30 of FIG. 7, in accordance with embodiments of the present invention. The cross section of the filter 30 in FIG. 8 depicts a layered structure 48 interior to the bounding surface 35 of the filter 30. The layered structure 48 comprises: a charcoal layer 41 within the filter 30 at the outer surface 35 of the filter 30; a coating 42 on and in direct mechanical contact with the activated charcoal layer 41; and a heparin layer 43 on and in direct mechanical contact with the coating 42. The charcoal layer 41 is on and in direct mechanical contact with the bounding surface 35 of the filter 30 such that the bounding surface 35 surrounds the charcoal layer 41. The charcoal layer 41 comprises activated charcoal and is an example of a carbon structure.

The coating 42 is disposed between the activated charcoal layer 41 and the heparin layer 43. The coating 42 comprises or consists of cellulose, polymethylmethacrylate (PMMA), polyethylmethacrylate (PEMA), or polyhydroxyethylmethacrylate (PHEMA).

The heparin layer 43 comprises heparin or a heparin derivative such as low molecular weight heparin. The anticoagulant property of heparin prevents the blood from clotting. Thus, the heparin layer 43 may eliminate the systemic administration of heparin to patients undergoing renal dialysis as well as for other medical procedures in which the filtration system 10 is used to remove a contaminant such as, inter alia, wastes, toxins, viruses, unwanted chemicals, etc from the blood.

If the bounding surface 35 of the cross section of the filter is circular in shape, then the cross-section of the filter is characterized by a radius R from the center 44 of the filter cross section to the outer surface 35. Denoting the combined radial thickness of the activated charcoal layer 41, the coating 42, and the heparin layer 43 as T, the relationship between T and R in one embodiment is: $0.05 \leq T/R \leq 0.15$. Denoting the radial thickness of the activated charcoal layer 41 as $T_{AC}$, the radial thickness of the coating 42 as $T_{COAT}$, and the radial thickness of the heparin layer 43 as $T_{HEP}$, the following radial thickness relationships exist in one embodiment:

$$0.20T \leq T_{HEP} \leq 0.30T;$$

$$0.70T \leq T_{HEP} + T_{COAT} \leq 0.80T;$$

$$2.0 \leq T_{AC}/T_{COAT} \leq 1.7; \text{ and}$$

$$T_{AC} + T_{COAT} + T_{HEP} = T.$$

The blood traverses the filter through the flow area 45 of the filter 30. The flow area 45 is bounded by the heparin layer 43 and comprises space in the filter's cross section not occupied by the layered structure 48. The layered structure 48 is configured to remove a contaminant in a flowing liquid (e.g., a biological fluid) as the flowing liquid flows through the filter 30 in a direction normal to the flow area 45.

Figure 9:
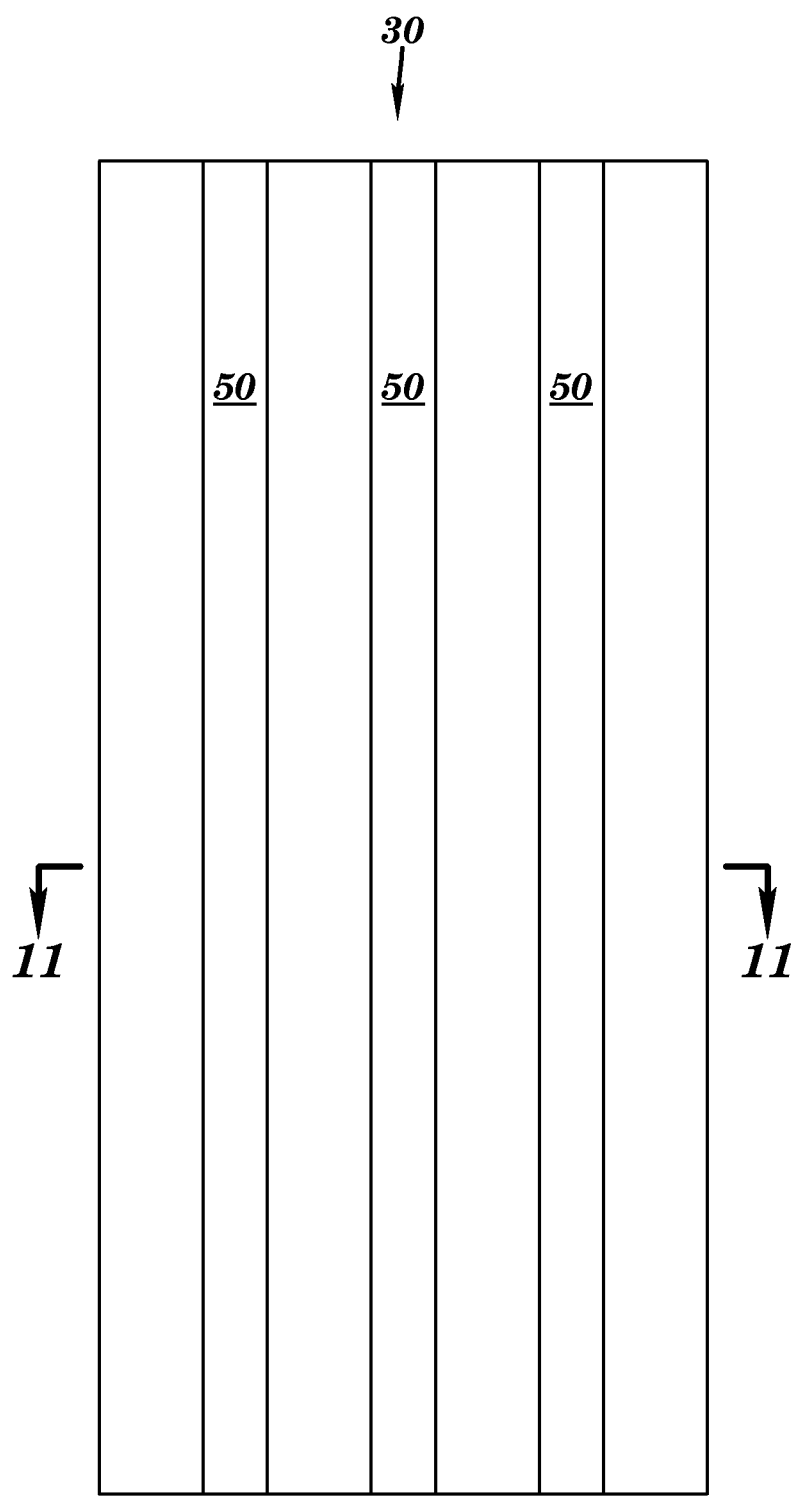
FIG. 9 depicts the filter of FIG. 7 with at least one carbon nanotube in the filter, in accordance with embodiments of the present invention.

FIG. 9 depicts the filter 30 of FIG. 7 with at least one carbon nanotube 50 in the filter 30, in accordance with embodiments of the present invention. The carbon nanotube(s) 50 are parallel to each other and are aligned in the direction of the blood flow (i.e., in the direction between the valves 31 and 32). In FIG. 9, the nanotube(s) in the filter 30 may consist of one carbon nanotube, two carbon nanotubes, or a plurality of carbon nanotubes 50 (e.g., 2, 3, 4, 5, . . . etc. carbon nanotubes). A carbon nanotube is an example of a carbon structure.

Figure 10:
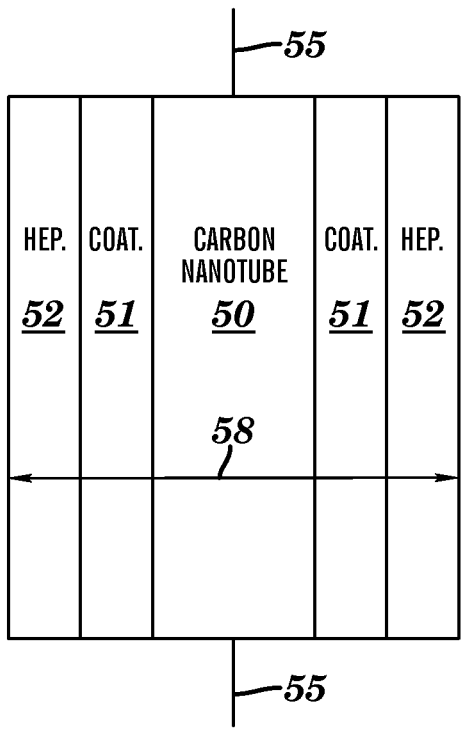
FIG. 10 depicts a carbon nanotube from the filter of FIG. 9 with a layered structure, in accordance with embodiments of the present invention.

FIG. 10 depicts a carbon nanotube 50 from the filter of FIG. 9 with a layered structure 58, in accordance with embodiments of the present invention. The layered structure 58 comprises: the carbon nanotube 50; a coating 51; and a heparin layer 52 disposed around the carbon nanotube 50. The coating 51 is external to the carbon nanotube 50 and surrounds the carbon nanotube 50. The coating 51 is on and in direct mechanical contact with the outer surface of the nanotube 50. The coating 51 is disposed between the carbon nanotube 50 and the heparin layer 52. The heparin layer 52 is on and in direct mechanical contact with the coating 51 and surrounds the coating 51. The coating 51 comprises cellulose, PMMA, PEMA, or PHEMA. The heparin layer 52 comprises heparin or a heparin derivative such as low molecular weight heparin.

When the coating 51 comprises PMMA, the heparin layer 52 is conjugated to the PMMA of the coating 51 through the PMMA's free amino groups.

When the coating 51 comprises cellulose, the heparin-cellulose-activated charcoal composites may be formed using room temperature ionic liquids (RTILs) to enhance the biocompatibility and blood compatibility of the activated charcoal while decreasing the size of the active pores of the activated charcoal. The RTILs consist entirely of ionic species.

The carbon nanotube(s) 50 in FIGS. 9 and 10 represent an alternative embodiment that exists in the filter 30 instead of the layers 41, 42, and 43 in the embodiment of FIG. 8.

Figure 11:
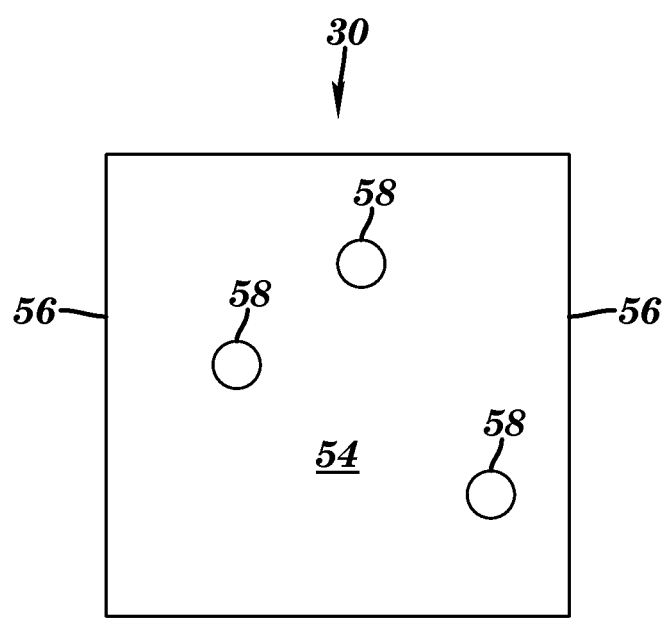
FIG. 11 is a cross-section view through line 11-11 of the filter of FIG. 9, in accordance with embodiments of the present invention.

FIG. 11 is a cross-section view through line 11-11 of the filter of FIG. 9, in accordance with embodiments of the present invention. The cross section of the filter 30 in FIG. 11 depicts the layered structures 58 of FIG. 10. The layered structures 58 are interior to the bounding surface 56 of the filter 30. The blood traverses the filter 30 through the flow area 54 of the filter 30. The flow area 54 comprises space in the filter's cross section not occupied by the layered structures 58. The layered structures 58 are configured to remove a contaminant in a flowing liquid (e.g., a biological fluid) as the flowing liquid flows through the filter 30 in a direction normal to the flow area 54.

The carbon structure of the present invention (e.g., the charcoal layer 41 of FIG. 8; the carbon nanotube 50 of FIGS. 9 and 10), on which the coating layer and heparin layer are disposed, may have any geometric shape (films, fibers, spheres, cylinders, tubes, annuli, etc.).

The bounding surface in the cross section of the filter 30 (e.g., the bounding surface 35 of FIG. 8; the bounding surface 56 of FIG. 11) may have any geometrical shape such as a circle, ellipse, polygon, etc.

Figure 12:
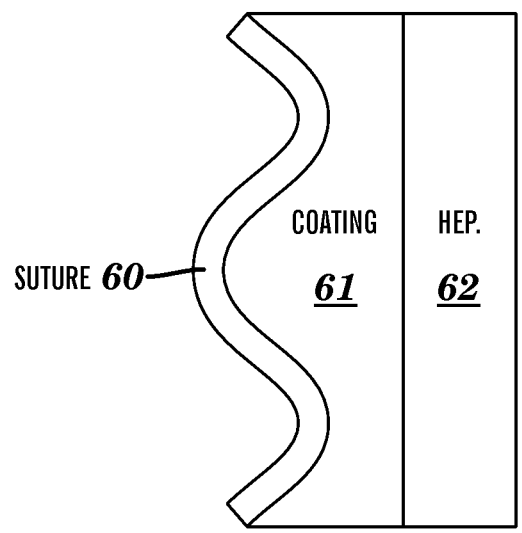
FIG. 12 depicts a suture with layers of cellulose and heparin disposed on the suture, in accordance with embodiments of the present invention.

FIG. 12 depicts a suture 60 with a coating 61 and a heparin layer 62 disposed on the suture 60, in accordance with embodiments of the present invention. The coating 61 is on and in direct mechanical contact with the suture 60. The heparin layer 62 is on and in direct mechanical contact with the coating. The coating 61 is disposed between the suture 60 and the heparin layer 62. The coating 51 comprises cellulose, PMMA, PEMA, or PHEMA. The heparin layer 62 comprises heparin or a heparin derivative such as low molecular weight heparin.

Figure 13:
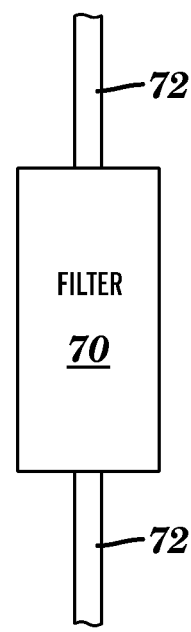
FIG. 13 depicts a filter is series with piping in a plumbing system, in accordance with embodiments of the present invention.

FIG. 13 depicts a filter 70 in series with piping 72 in a plumbing system, in accordance with embodiments of the present invention. In one embodiment, the filter 70 of FIG. 13 is the same as the filter 30 of FIG. 8, except that there is no heparin layer 43. In one embodiment, the filter 70 of FIG. 13 is the same as the filter 30 of FIGS. 9-11, except that there is no heparin layer 52. The filter 70 may serve to purify water (i.e., remove toxins, chemicals, and other contaminants in the water) in the piping 72 in the plumbing system of a house, apartment, commercial office, factory, etc.

Figure 14:
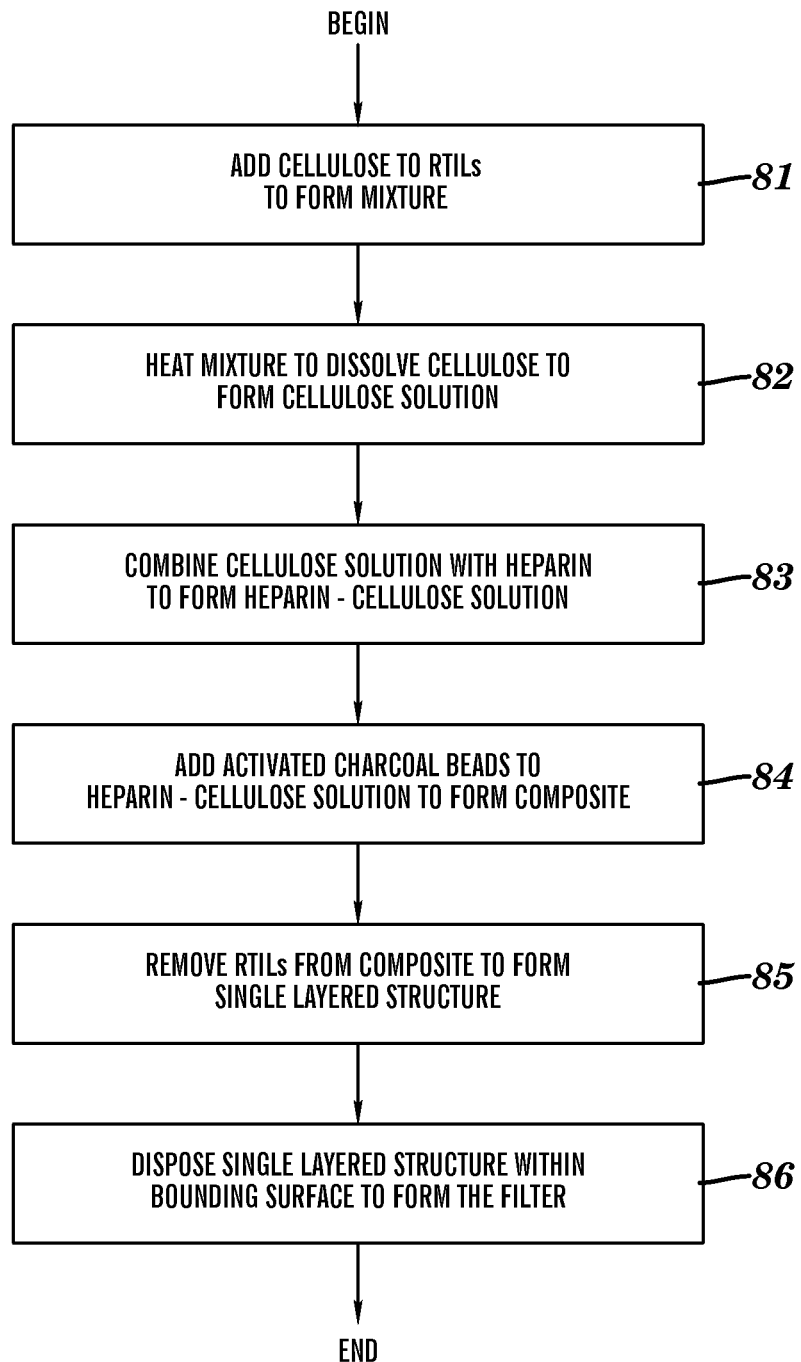
FIG. 14 is a flow chart depicting a method of forming a filter, in accordance with embodiments of the present invention.

FIG. 14 is a flow chart depicting a method of forming a filter, in accordance with embodiments of the present invention. The method of FIG. 14 includes steps 81-88.

Step 81 adds cellulose to room temperature ionic liquids (RTILs) to form a mixture.

Step 82 heats the mixture to dissolve the cellulose to form a cellulose solution.

Step 83 combines the cellulose solution with heparin to form a heparin-cellulose solution.

Step 84 adds activated charcoal beads to the heparin-cellulose solution to form a composite of charcoal beads coated with the heparin-cellulose solution.

Step 85 processes the composite to form the single layered structure, which includes removing the RTILs from the composite.

Step 86 disposes the single layered structure within the bounding surface such that the charcoal layer is on and in direct mechanical contact with the bounding surface and the bounding surface surrounds the charcoal layer, which results in formation of the filter While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A filter, comprising:
   at least one layered structure interior to an outermost bounding surface of the filter;
   wherein each layered structure comprises a carbon structure, a coating totally external to and having an outermost bounding surface in direct mechanical contact with an innermost bounding surface of the carbon structure, and a heparin layer having an outermost bounding surface in direct mechanical contact with an innermost bounding surface of the coating;
   wherein the carbon structure comprises carbon;
   wherein the coating comprises a coating material consisting of cellulose or a methacrylate selected from the group consisting of polymethylmethacrylate (PMMA), polyethylmethacrylate (PEMA), and polyhydroxyethylmethacrylate (PHEMA);
   wherein the heparin layer comprises heparin;
   wherein the layered structure is configured to remove a contaminant in a flowing liquid as the flowing liquid flows through the filter by flowing through a flow area of the filter;
   wherein the carbon structure surrounds the entire coating;
   wherein the coating is totally external to, disposed between, and in direct mechanical contact with, the heparin layer and the carbon structure;
   wherein an innermost bounding surface of the heparin layer coincides with an outermost bounding surface of the flow area; and
   wherein the heparin layer is totally external to, disposed between, and in direct mechanical contact with, the flow area and the coating.

2. The filter of claim 1, wherein the carbon structure is on and in direct mechanical contact with the outermost bounding surface of the filter such that the outermost bounding surface surrounds the carbon structure.

3. The filter of claim 1, wherein the carbon structure in each layered structure is a carbon nanotube such that the coating is external to the carbon nanotube.

4. The filter of claim 3, wherein the at least one layered structure consists of a plurality of layered structures.

5. The filter of claim 1, wherein the carbon structure in each layered structure is a sphere.

6. The filter of claim 1, wherein the coating material consists of said cellulose.

7. The filter of claim 1, wherein the coating material consists of said methacrylate.

8. A method of removing contamination from a biological fluid of a mammal, said method comprising:
   flowing the biological fluid from the animal through the filter of claim 1, which results in the filter removing a portion of the contamination from the biological fluid, wherein the biological fluid is the flowing liquid.

9. The method of claim 8, wherein the biological fluid is blood.

10. The method of claim 9, wherein the contamination is a chemotherapy drug in the blood resulting from an organ of the mammal being treated for cancer by the chemotherapy drug.

11. The method of claim 10, wherein the organ of the mammal is a liver of the mammal, a pancreas of the mammal, a kidney of the mamma, or a lung of the animal.

12. The method of claim 9, wherein the contamination is metabolic waste, and wherein the blood is being flowed through the filter in conjunction with renal dialysis being administered to the mammal.

13. The method of claim 9, wherein the contamination is a poison or alcohol.

14. The method of claim 8, wherein the mammal is a human being.

15. The method of claim 8, wherein the mammal is a non-human mammal.

16. A filter, comprising:
   a layered structure interior to an outermost bounding surface of the filter;

wherein the layered structure comprises a charcoal layer, a coating totally external to and having an outermost bounding surface in direct mechanical contact with an innermost bounding surface of the charcoal layer, and a heparin layer having an outermost bounding surface in direct mechanical contact with an innermost bounding surface of the coating;

wherein the coating comprises a coating material consisting of cellulose or polymethylmethacrylate (PMMA);

wherein the heparin layer comprises heparin;

wherein the layered structure is configured to remove a drug in blood as the blood flows through the filter by flowing through a flow area of the filter;

wherein the charcoal layer surrounds the entire coating;

wherein the coating is totally external to, disposed between, and in direct mechanical contact with, the heparin layer and the charcoal layer;

wherein an innermost bounding surface of the heparin layer coincides with an outermost bounding surface of the flow area; and wherein the heparin layer is totally external to, disposed between, and in direct mechanical contact with, the flow area and the coating.

17. The filter of claim 16, wherein the coating material consists of said cellulose.

18. The filter of claim 16, wherein the coating material consists of said methacrylate.

19. A method of removing a drug from blood of an animal, said method comprising:

flowing the blood of the animal through the filter of claim 16, which results in the filter removing a portion of a quantity of the drug from the blood, wherein the animal is a human being or a bovine animal.

20. The method of claim 19, wherein the drug is a chemotherapy drug in the blood resulting from a liver of the animal being treated for cancer by the chemotherapy drug.

21. The method of claim 19, wherein the animal is said human being.

22. The method of claim 19, wherein the animal is said bovine animal.

23. A method of forming the filter of claim 16, wherein the coating material consists of said cellulose, and wherein the method comprises:

adding cellulose to room temperature ionic liquids (RTILs) to form a mixture;

heating the mixture to dissolve the cellulose to form a cellulose solution;

combining the cellulose solution with heparin to form a heparin-cellulose solution;

adding activated charcoal beads to the heparin-cellulose solution to form a composite of charcoal beads coated with the heparin-cellulose solution;

processing the composite to form the layered structure, said processing comprising removing the RTILs from the composite; and disposing the layered structure within the outermost bounding surface of the filter such that the charcoal layer is on and in direct mechanical contact with the outermost bounding surface of the filter and the outermost bounding surface of the filter surrounds the charcoal layer, which results in formation of the filter.

24. The filter of claim 1, wherein a center of the filter is within the flow area, and wherein the coating is disposed between the center of the filter and the carbon structure.

\* \* \* \* \*